(12) United States Patent
Parker et al.

(10) Patent No.: US 8,628,978 B2
(45) Date of Patent: Jan. 14, 2014

(54) RESPONSIVE LUMINESCENT LANTHANIDE COMPLEXES

(75) Inventors: David Parker, Durham (GB); Robert Pal, Durham (GB)

(73) Assignee: University of Durham, Durham (GB)

( * ) Notice: Subject to any disclaimer, the term of this patent is extended or adjusted under 35 U.S.C. 154(b) by 149 days.

(21) Appl. No.: 13/145,849

(22) PCT Filed: Jan. 29, 2010

(86) PCT No.: PCT/GB2010/000147
§ 371 (c)(1),
(2), (4) Date: Jul. 22, 2011

(87) PCT Pub. No.: WO2010/086615
PCT Pub. Date: Aug. 5, 2010

(65) Prior Publication Data
US 2011/0287558 A1 Nov. 24, 2011

(30) Foreign Application Priority Data

Jan. 30, 2009 (GB) .................................. 0901556.1

(51) Int. Cl.
*G01N 21/63* (2006.01)
*C07D 257/02* (2006.01)
*C07D 495/04* (2006.01)
*C09K 11/06* (2006.01)

(52) U.S. Cl.
USPC ............ 436/501; 540/465; 540/470; 540/474

(58) Field of Classification Search
None
See application file for complete search history.

(56) References Cited

FOREIGN PATENT DOCUMENTS

| WO | 2006/039505 A2 | 4/2006 |
|----|----|----|
| WO | 2006/120444 A1 | 11/2006 |
| WO | 2008/007089 A1 | 1/2008 |
| WO | 2008/132433 A1 | 11/2008 |

OTHER PUBLICATIONS

B.H. Bakker, et al., Luminescent materials and devices: lanthanide azatriphenylene complexes and electroluminescent charge transfer systems, Coord. Chem. Rev., 2000, 208, pp. 3-16.
JC.G. Bunzli, et al., Taking advantage of luminescent lanthanide ions, Chem. Soc. Rev.; 2005, 34, pp. 1048-1077.
S. Petoud, et al., Stable Lanthanide Luminescence Agents Highly Emissive in Aqueous Solution: Multidentate 2-Hydroxyisophthalamide Complexes of Sm3+, Eu3+, Tb3+, Dy3+, J. Am. Chem. Soc., 2003, 125, pp. 13324-13325.
A. Dadabhoy, et al., Small singlet-triplet energy gap of acridone enables longer wavelength sensitisation of europium (III) luminescence, J. Chem. Soc. Perkin Trans. 2, 2000, pp. 2359-2360.

J. Yu, et al., Synthesis of a Europium Complex for Anion-Sensing Involving Regioselective Substitution of Cyclen, Eur. J. Org. Chem., 2005, pp. 4249-4252.
P. Atkinson, et al., Azaxanthones and azathioxanthones are effective sensitisers for europium and terbium luminescense, Org. Biomol. Chem., 2006, 4, pp. 1707-1722.
E.A. Schell-Feith, et al., Does citrate prevent nephrocalcinosis in preterm neonates?, Pediatric Nephrol., 2006, 21, pp. 1830-1836.
V. Cebotaru, et al., High citrate diet delays progression of renal insufficiency in C1C-5 knockout mouse model of Dent's disease, Kidney Int., 2005, vol. 68, pp. 642-652.
L. C. Costello, et al., The clinical relevance of the metabolism of prostate cancer; zinc and tumor suppression: connecting the dots, Molecular Cancer, 2006, 5:17, 13 pages.
LC Costello, et al., Prostatic fluid electrolyte composition for the screening of prostate cancer: a potential solution to a major problem, Prostate Cancer and Prostatic Diseases, 2009, 12, pp. 17-24.
R. S. Dickins, et al., Structural, Luminescence, and NMR Studies of the Reversible Binding of Acetate, Lactate, Citrate, and Selected Amino Acids to Chiral Diaqua Ytterbium, Gadolinium, and Europium Complexes, J. Am. Chem. Soc., 2002, 124, pp. 12697-12705.
International Search Report and Written Opinion, International Application No. PCT/GB2010/000147, Mar. 30, 2010.
Palsson, Lars-Olof et al., "Two-photon absorption and photoluminescence of europium based emissive probes for bioactive systems", Dalton Transactions, 2007, pp. 5726-5734.
Yu, Junhua et al., "A Europium Complex That Selectively Stains Nucleoli of Cells", Journal of the American Chemical Society, 2006, pp. 2294-2299, 128(7).
Pal, Robert et al., "A ratiometric optical imaging probe for intracellular pH based on modulation of europium emission", Organic & Biomolecular Chemistry, 2008, pp. 1020-1033, 6(6).
Pal, Robert et al., "A europium luninescence assay of lactate and citrate in biological fluids", Organic & Biomolecular Chemistry, 2009, pp. 1525-1528, 7(8).
Parker et al, "A pH-insensitive, ratiometric chemosensor for citrate using europium luminescence", Chemical Communications, 2005, pp. 3141-3143, Issue 25.

*Primary Examiner* — Shafiqul Haq
*Assistant Examiner* — Galina Yakovleva
(74) *Attorney, Agent, or Firm* — Berenato & White, LLC

(57) ABSTRACT

A compound of formula (I) is provided:

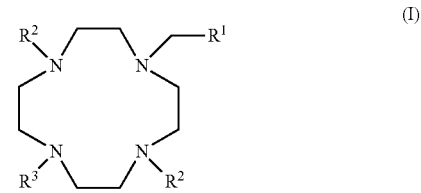

(I)

wherein:
  $R^1$ is an optionally substituted 2-(1-azathiaxanthone);
  each $—R^2$ is independently of the formula $—CH_2—C(=O)—R^4$, wherein $R^4$ is an amino acid or a salt thereof, attached to the remainder of $R^2$ through the nitrogen atom of the amino group; and
  $R^3$ is hydrogen or a $C_{1-6}$ alkyl group; or
wherein:
  $R^1$ is an optionally substituted 2-(1-azaxanthone);
  each $R^2$ is independently an optionally substituted glutaric or succinic acid, or a salt or ester thereof; and
  $R^3$ is hydrogen or a $C_{1-6}$ alkyl group.

29 Claims, 10 Drawing Sheets

RESPONSIVE LUMINESCENT LANTHANIDE COMPLEXES

CROSS REFERENCE TO RELATED APPLICATIONS

The present application is the national stage under 35 U.S.C. 371 of international application PCT/GB2010/000147, filed Jan. 29, 2010, which designated the United States, was published under PCT Article 21(2) in the English language, and claims the benefit of priority of United Kingdom patent application 0901556.1 filed Jan. 30, 2009.

FIELD OF THE INVENTION

This invention provides luminescent lanthanide complexes, methods for their efficient sensitisation and their use in assays of bioactive species, for example present in biological fluids, e.g. solutions and in the diagnosis of certain medical conditions associated with abnormal quantities of citrate or lactate.

INTRODUCTION

The unique magnetic and spectroscopic properties of the ground and excited states of the f block ions afford considerable scope for the development of new chemical entities that can be used as imaging probes, as components of optoelectronic devices, or as key sensor materials. Particular advantages of f-block ions are their intense, line-like and long-lived luminescence at a range of wavelengths spanning the visible and near infrared (NIR) regions, which permits time-gated rejection of unwanted signals arising from (short-lived) autofluorescence from biomolecules. Lanthanide chemistry accordingly plays a key role in such diverse areas as display technology and clinical diagnosis.

There is a need for simple modular synthetic routes that lead to stable emissive systems with tunable photophysical properties and high overall quantum yields (>10% for Eu/Tb in competitive media), that resist photo-fading and bleaching, and can be excited at longer wavelengths to minimise competitive absorption by endogenous molecules or tissue (at the very least, they should obviate the use of quartz optics). Moreover, they should, preferably, allow scope for conjugation to biomolecules, and should, preferably, be compatible with other probes to permit multiplexed imaging. Notwithstanding the burgeoning academic literature (e.g. Verhoeven, Bunzli, Raymond and Sammes (for example B H Bakker et al., *Coord. Chem. Rev.*, 2000, 208, 3; JCG Bunzli & C. Piguet, *Chem. Soc. Rev.*, 2005, 34, 1098; S. Petoud et al., *J. Am. Chem. Soc.*, 2003, 125, 13324; and A. Dadabhoy et al., *J. Chem. Soc. Perkin Trans* 2, 2000, 2359) reporting the chemistry of new emissive lanthanide (III) complexes or probes, no single molecule meets each of these criteria, and new approaches are required.

Moreover, organic chromophores have been widely used as sensitisers of lanthanide emission. However, very few of these possess a $S_1$-$T_1$ energy gap small enough to allow excitation at the longest possible wavelengths without detrimental back energy transfer from the excited state of the metal ion to the sensitiser $T_1$ state. This is a particularly demanding task for the visibly emitting lanthanides, since their high excited state energies restrict the range of possible sensitisers to those with relatively high triplet state energies. Acridones have been used for this purpose, but in polar media possess an inefficient inter-system crossing step, so that sensitiser fluorescence competes with triplet formation.

In WO2006/120444 (University of Durham) it is reported that a number of lanthanide complexes described therein (incorporating azaxanthone and azathiaxanthone sensitisers) undergo efficient sensitized excitation and can be used in time-resolved assays of bioactive species, especially in signalling the variation in the local concentration of endogenous species. Similar or the same complexes and macrocyclic ligands are also reported by D. Parker and J. Yu (*Chem. Commun.* 2005, 3141-3143); J. Yu and D. Parker (*Eur. J. Org. Chem.*, 2005, 4249-4252); and P. Atkinson et al., *Org. Biomol. Chem.*, 2006, 4, 1707-1722).

Two examples of such endogenous species present in biological fluids, and of particular interest, are the oxy anions citrate and lactate.

The citrate anion exists in all living cells. It is not only an important intermediate in the tricarboxylic acid cycle, but also a key component of fatty acid, cholesterol and hormone synthesis, photorespiration, the glyoxylate cycle and nitrogen metabolism. Due to its metabolic significance, abnormal citrate levels have been linked to the characteristics of several diseases. For example, citrate concentration in urine can reflect renal metabolic imbalance. Decreased urinary citrate excretion has been shown to be important in the pathogenesis of nephrocalcinosis and nephrolithiasis (E. A. Schell-Feit et al., *Pediatric Nephrol.*, 2006, 21, 1830; V. Cebotaru et al., *Kidney Int.*, 2005, 68, 642. 3.). Recently, citrate has been selected as a marker for the discrimination of prostate cancer as a result of the highly specialized anatomical function of the prostate gland (L. C. Costello and R. B. Franklin, *Mol Cancer.* 2006, 5, 17; and L. C. Costello and R. B. Franklin. *Prostate Cancer Prostatic Dis.* 2008, Jul. 1.).

The main function of the prostate gland is to secrete and store a clear fluid (pH 7.3) that constitutes about 50% of the volume of the seminal fluid that, along with spermatozoa, constitutes the semen. The prostatic fluid is mainly composed of simple sugars, less than 1%, and protein including the prostate-specific antigen (PSA). The secretion also contains various amounts of zinc and sodium citrate, whose concentration changes significantly as a function of malignancy of the epithelial tissue that makes up this part of the male reproductive organ. Prostate cancer (PCa) is the most common non-skin related male cancer type in the world, affecting one in ten men in the UK. It is classified as adenocarcinoma; PCa begins when normal semen-secreting prostate gland cells mutate into cancer cells. These may lead to formation of a tumour and eventually, if not recognised, invade nearby organs. As the tumour cells may develop the ability to travel in the bloodstream and lymphatic system causing metastasis, PCa is considered as a malignant disease.

Prostate secretory epithelial cells have the specialised function and capability of accumulating and secreting extraordinarily high levels of citrate. This is achieved by the existence of a zinc-inhibited low mitochondrial aconitase (m-Ac) activity that minimises the ability of the cell to oxidise citrate via the Krebs cycle. Consequently, citrate synthesised by these cells is accumulated and secreted, thereby accounting for the extremely high (20-200 mM) citrate content of human prostatic fluid, compared with the low values (0.1-0.4 mM) in typical mammalian cells. The level of prostate m-Ac enzyme appears to be similar to that associated with other cells, although the levels of m-Ac activity and consequent citrate oxidation are significantly lower in prostate cells.

Prostate epithelial cells normally possess uniquely high cellular and mitochondrial zinc levels. Studies have shown that zinc inhibition of the m-Ac activity accounts for the minimised citrate oxidation and consequently the high citrate level which characterises prostate cells. The diminished ability of neoplastic epithelial cells, mainly in the peripheral zone of the prostate, to accumulate zinc (80% decrease in $C_{Zn}$) is a consistent factor in their development of malignancy and the subsequent dramatic decrease in prostatic citrate concentration. The variation of citrate levels is striking, and is believed to lead to a reduction from 180 mM (healthy patients) to around 10 mM as disease progresses.

Prostate cancer screening is an attempt to detect unsuspected cancers in their earliest stages. As PCa is a slow-growing cancer, the chances to identify the disease in early stage are high. A major problem involved in prostate cancer (PCa) diagnosis is the absence of sensitive, accurate, and preferably non-invasive early diagnostic procedures. The current diagnostic and screening procedures (e.g. the prostate specific antigen test) are considered to be highly inaccurate. Therefore, there is a need for a uniform, well-established and non-invasive screening procedure. Citrate level tests from prostate or seminal fluid samples may overcome the risk and inaccuracy of current screening procedures.

One main drawback of citrate level measurement in the prostate fluid is that obtaining the sample requires a biopsy. Prostate fluid, as the main source (about 50%), gives rise to seminal fluid citrate level of about 20-60 mM. The high citrate content of seminal fluid is consistent with its function as a buffer to maintain the pH of semen. It may also serve as a chelator for zinc and other divalent cations which are highly concentrated and involved in liquefaction of semen, as well as serving as an energy source for sperm maturation and viability. Its role may be complex, but importantly the citrate level in seminal fluid is proportionate to that in the prostate fluid. Therefore, citrate level measurements from seminal fluid samples could aid the detection of prostate malignancy, in particular, analysis of citrate concentration of expressed prostatic fluid can provide a simplified, accurate and relatively non-invasive screening procedure useful in the diagnosis of prostate cancer. (L. C. Costello and R. B. Franklin. *Prostate Cancer Prostatic Dis.* 2008, Jul. 1, infra).

It is also notable that a sensor possessing an appropriate citrate affinity may be used to analyse urine samples. This may aid in the detection of any renal anomaly, such as urolithic kidney dysfunction or nephrolithiasis, as the citrate concentration in urine (about 4 mM in a healthy patient) may be significantly increased.

Lactic acid (2-hydroxypropanoic acid) is a chemical compound that plays a significant role in several biochemical processes. It is a chiral alpha hydroxy acid. The concentration of blood lactate in humans is usually 1-2 mM at rest, but can rise to over 20 mM during intense exertion. Lactic acid has two enantiomeric forms, L(+) and D(−); L(+)-lactic acid is the naturally occurring isomer and is present in the human body. Lactic acid is a weak acid ($pK_a$=3.86) and under physiological conditions the majority of lactic acid is present as lactate anion.

Lactic acid is naturally present in many foodstuffs and is formed by natural fermentation in products. It is also used in a wide range of food applications such as bakery products, beverages, meat products, confectionery, dairy products, salads, dressings and ready meals. Lactic acid in food products usually serves as either as a pH regulator, preservative or as a flavouring agent (E270). It also has several other important applications and roles in many aspects of our daily life, such as pharmaceutical and cleansing products or as a precursor for biodegradable polymers. In animals and humans, L-lactate is constantly produced from pyruvate via the enzyme lactate dehydrogenase (LDH) in a process of fermentation during normal metabolism and exercise. It is well known that it is formed from glycogen by muscle cells when the oxygen supply is inadequate to support energy production. Accumulation of lactic acid in the muscle, occurs only during short bouts of exercise of relatively high intensity, is often related to fatigue and muscle soreness. Lactic acid levels also increase in conditions such as heart failure, severe infection (sepsis), or shock. In each case, the flow of blood and oxygen throughout the body is lowered. Lactic acid levels are also elevated when the liver is severely damaged or diseased, because the liver normally breaks down lactic acid. Very high levels of lactic acid may cause a serious, sometimes life-threatening condition termed lactic acidosis. Due to its key role not only in everyday products but also in the human body, the development of a single component, fast response lactic acid sensor is needed. The assay is of particular importance for confirmation of the hypothesis (Warburg effect) of elevated lactic acid levels in malignant (cancerous) tissue samples and/or biological fluids.

Current commercially available (L−) lactic acid assays are based on enzymatic methods. The quantification of L-lactic acid requires two enzyme reactions catalysed by L-lactate dehydrogenase (L-LDH), where L-lactate is oxidised to pyruvate by nicotinamide-adenine dinucleotide ($NAD^+$), (Eq. 1)

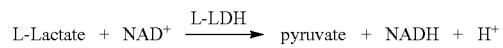

(Eq. 1)

$$\text{L-Lactate} + NAD^+ \xrightarrow{\text{L-LDH}} \text{pyruvate} + NADH + H^+$$

However, since the equilibrium of Eq. 1 lies firmly in favour of L-lactic acid and $NAD^+$, a further reaction is required to 'trap' the pyruvate product. This is achieved by the conversion of pyruvate to D-alanine and 2-oxoglutarate, using the enzyme D-glutamate-pyruvate transaminase (D-GPT) in the presence of a large excess of D-glutamate, (Eq. 2).

(Eq. 2)

$$\text{Pyruvate} + \text{D-glutamate} \xrightarrow{\text{D-GPT}} \text{D-alanine} + \text{2-oxoglutarate}$$

The amount of NADH formed in the above coupled reaction is stoichiometric with respect to L-lactic acid. It is the NADH which is measured by an increase in absorbance at 340 nm. The assay is specific to L-lactic acid and linear over the range of 0 to 3.3 mM; more concentrated samples requires dilution prior to analysis. The smallest differentiation in absorbance for the assay is 0.01 absorbance units. This corresponds to a 2.4 micromolar difference in L-lactic acid concentration in the solution (with a sample volume of 1.5 mL).

This method of analysis has been found to be sensitive to certain interferents. Analysis of acidic samples should be performed after raising sample pH to 10 (using NaOH), following incubation for 30 min. Samples containing carbon dioxide, need to be degassed by increasing to pH to 10 with constant stirring. Coloured samples may also cause interference. Strongly coloured samples require treatment by a combination of surface adsorbents and filtration. Samples containing fat requires elimination of any solid components and clarification. Samples containing protein require elimination (digestion and filtration or centrifugation) of any high molecular weight material. Thus, whilst the method is accurate, it is based on a relatively insensitive measurement of absorbance at 340 nm. The need to treat certain samples prior to analysis adds complexity. As with any UV absorbance-based method, a reasonable amount of sample is required to execute a measurement. This feature combined with the observed insensitivity below L-lactic acid at levels of 0.5 mM prevents the assessment of any biological fluid with a small sample volume or a low lactic acid concentration. Being a four-component enzymatic assay kit, it also requires time and care to set up, and the kit requires cold storage (−20° C.) and rather long data acquisition times (sometimes up to 30 min reaction time involving 3-4 readings).

There remains a need to develop simple chemoselective methods to determine the concentration of these oxyanions—i.e. citrate and lactate—in biological fluids such as serum, urine and prostate or seminal fluid samples.

Considering the analysis of citrate and lactate in bio-fluids, a single-component, fast response sensor for each species is desirable. This should ideally possess the following characteristics: tuneable affinity for the target analyte; insensitivity to common interferences found in typical bio-fluid samples such as anions, proteins and certain cations (e.g. $Ca^{2+}$, $Zn^{2+}$ and $Mg^{2+}$) that perturb the equilibrium speciation; allow multiple readings using emission spectral techniques, preferably in the visible or near-visible range of the spectrum; and capability to operate on small sample volumes.

SUMMARY OF THE INVENTION

We have surprisingly found that lanthanide complexes of certain macrocycles are of particular utility in allowing selective detection of the citrate and lactate anions in a variety of liquid media. In particular, the present invention arises from the surprising finding that certain lanthanide complexes of azaxanthone- or azathiaxanone-derivatised macrocyclic ligands show specificity with regard to the reversible binding of citrate and lactate anions. We have thus found that a solution to the problem of measuring the concentration of certain citrate and lactate in biological fluids may be achieved with certain emissive lanthanide complexes, based on functionalised macrocyclic ligands, as defined herein, that are able to bind to citrate and lactate selectively and to signal this binding event by modulation of the metal-based emission, allowing (typically) ratiometric changes in band intensity to be monitored as a function of anion concentration. The affinity and selectivity profile of a given complex cannot be predicted precisely a priori, on account of the complex interplay between the effects of charge, steric demand and competitive ligation and the systems defined herein possess profiles that exhibit unexpectedly high selectivity for lactate or citrate respectively.

Viewed from a first aspect therefore the invention provides a compound of formula (I):

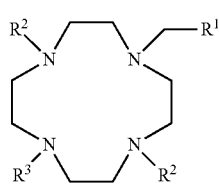

(wherein:
$R^1$ is an optionally substituted 2-(1-azathiaxanthone);
each $—R^2$ is independently of the formula $—CH_2—C(=O)—R^4$, wherein $R^4$ is an amino acid or a salt thereof, attached to the remainder of $R^2$ through the nitrogen atom of the amino group; and $R^3$ is hydrogen or a $C_{1-6}$ alkyl group); or
(wherein:
$R^1$ is an optionally substituted 2-(1-azaxanthone);
each $R^2$ is independently an optionally substituted glutaric or succinic acid, or a salt or ester thereof; and
$R^3$ is hydrogen or a $C_{1-6}$ alkyl group).

Viewed from a second aspect the invention provides a complex comprising a compound of formula (I) and a lanthanide ion, in particular a lanthanide (III) ion.

Viewed from a third aspect the invention provides the use of a complex of the invention, wherein $R^1$ is an optionally substituted 2-(1-azathiaxanthone); and each $—R^2$ is independently of the formula $—CH_2—C(=O)—R^4$, in the analysis of citrate present in a sample of interest. Complexes of the present invention of use in this aspect of the invention are referred to herein as comprising a compound of formula (Ia).

Viewed from a fourth aspect the invention provides the use of a complex of the invention, wherein $R^1$ is an optionally substituted 2-(1-azaxanthone); and each $R^2$ is independently an optionally substituted glutaric or succinic acid, or a salt or ester thereof, in the analysis of lactate present in a sample of interest. Complexes of the present invention of use in this aspect of the invention are referred to herein as comprising a compound of formula (Ib).

Viewed from a fifth aspect the invention provides a method of analysing citrate present in a sample of interest, the method comprising:
(i) contacting the sample of interest with a complex of the invention comprising a compound of formula (Ia);
(ii) exciting the azathiaxanthone; and
(iii) determining the quantity or concentration of any citrate in the sample of interest by analysis of the modulation in one or more emission bands resultant from the exciting where citrate is present.

Viewed from a sixth aspect the invention provides a method of analysing lactate present in a sample of interest, the method comprising:
(i) contacting the sample of interest with a complex of the invention comprising a compound of formula (Ib);
(ii) exciting the azaxanthone; and
(iii) determining the quantity or concentration of any lactate in the sample of interest by analysis of the modulation in one or more emission bands resultant from the exciting where citrate is present.

Viewed from a seventh aspect, the invention provides a method of, or for use in, the screening or diagnosis of prostate cancer comprising:
(i) obtaining a liquid sample from a subject;
(ii) optionally diluting the liquid sample; and
(iii) practising a method according to the fifth aspect of this invention, wherein the liquid sample or the diluted liquid sample constitutes the sample of interest.

Viewed from a eighth aspect, the invention provides a method of, or for use in, the screening or diagnosis of a renal anomaly comprising:
(i) obtaining a liquid sample from a subject;
(ii) optionally diluting the liquid sample; and
(iii) practising a method according to the fifth aspect of this invention, wherein the liquid sample or the diluted liquid sample constitutes the sample of interest.

Viewed from a ninth aspect, the invention provides a method of, or for use in, the screening or diagnosis of excessive lactic acid comprising:
(i) obtaining a liquid sample from a subject;
(ii) optionally diluting the liquid sample; and (iii) practising a method according to the sixth aspect of this invention, wherein the liquid sample or the diluted liquid sample constitutes the sample of interest.

Other aspects and embodiments of the invention will be apparent from the discussion and non-limiting exemplification of the invention that follows.

DETAILED DESCRIPTION OF THE INVENTION

Figure 1A:
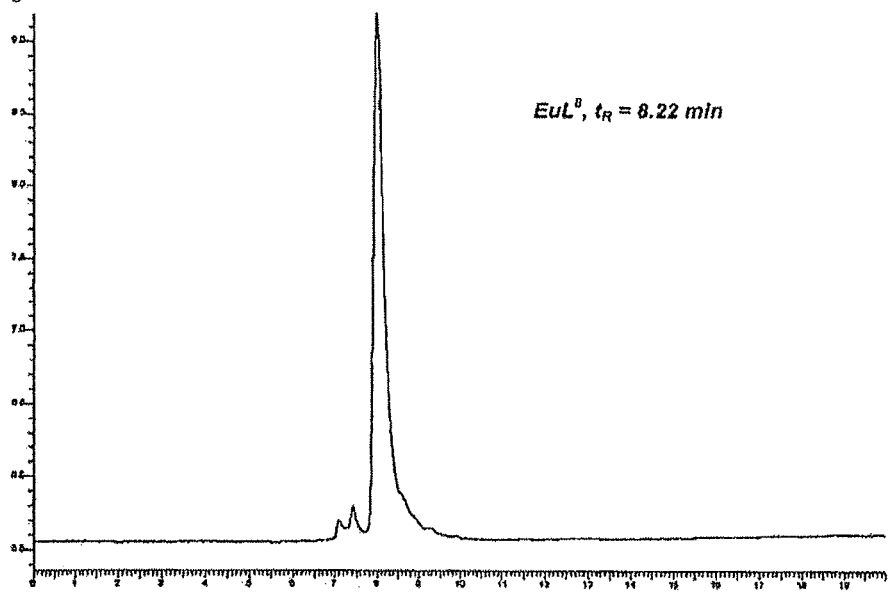
FIGS. 1A through 1I show variations representative LC chromatograms following HPLC analysis/purification of complexes of the invention and comparative complexes.
Figure 1B:
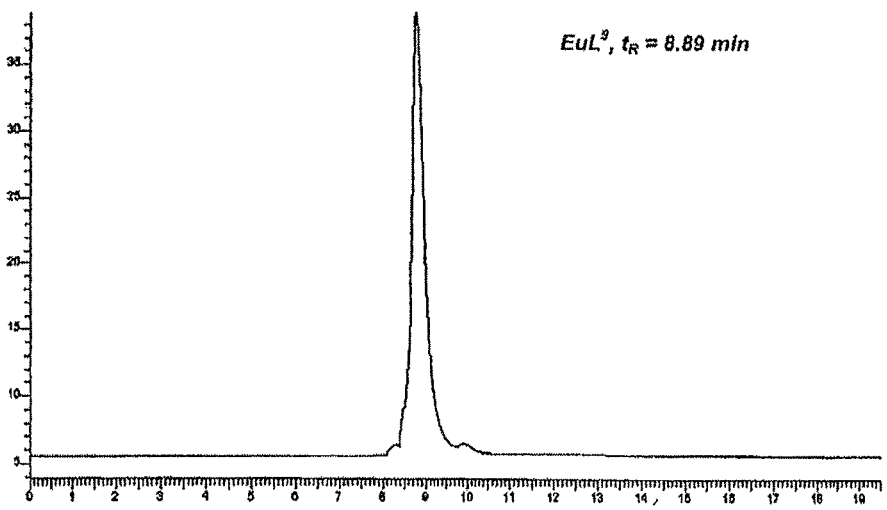
Figure 1C:
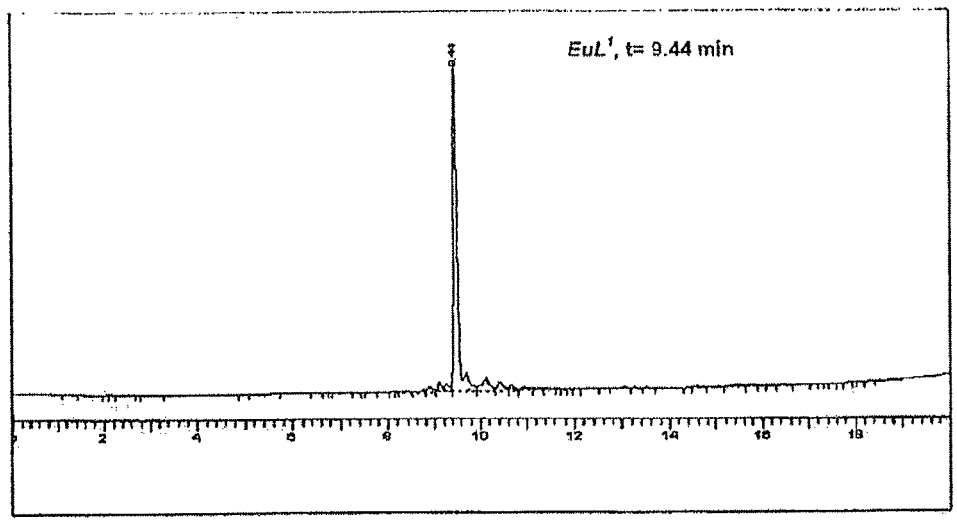
Figure 1D:
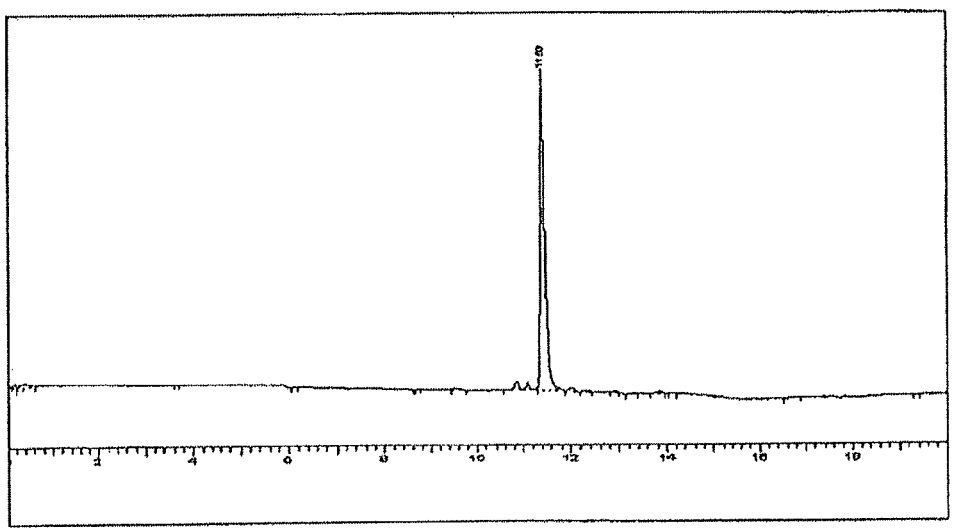
Figure 1E:
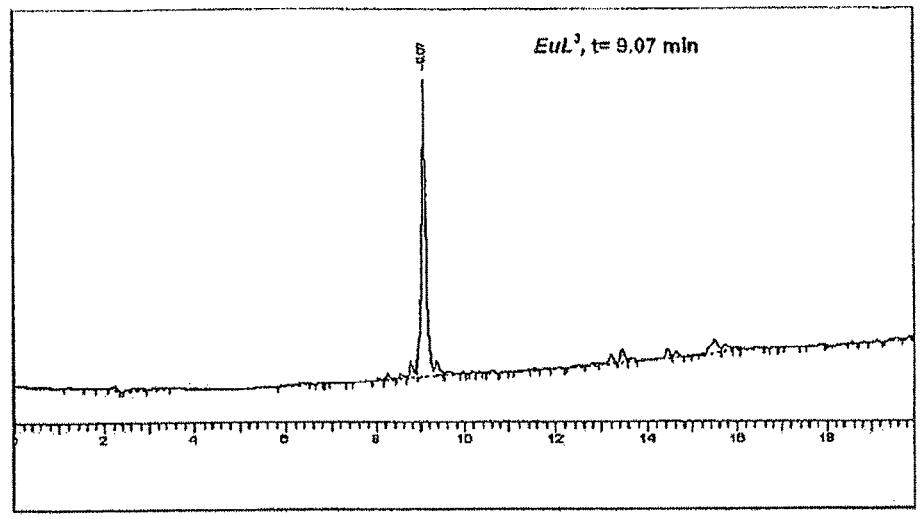
Figure 1F:
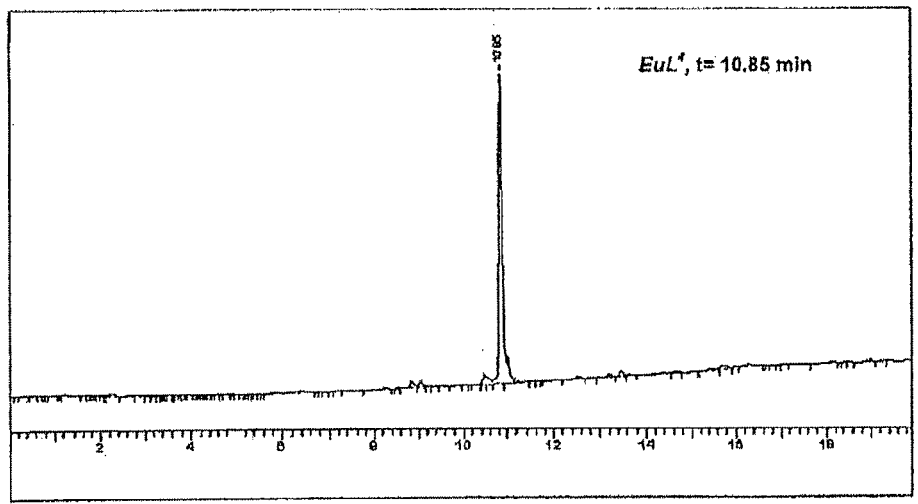
Figure 1G:
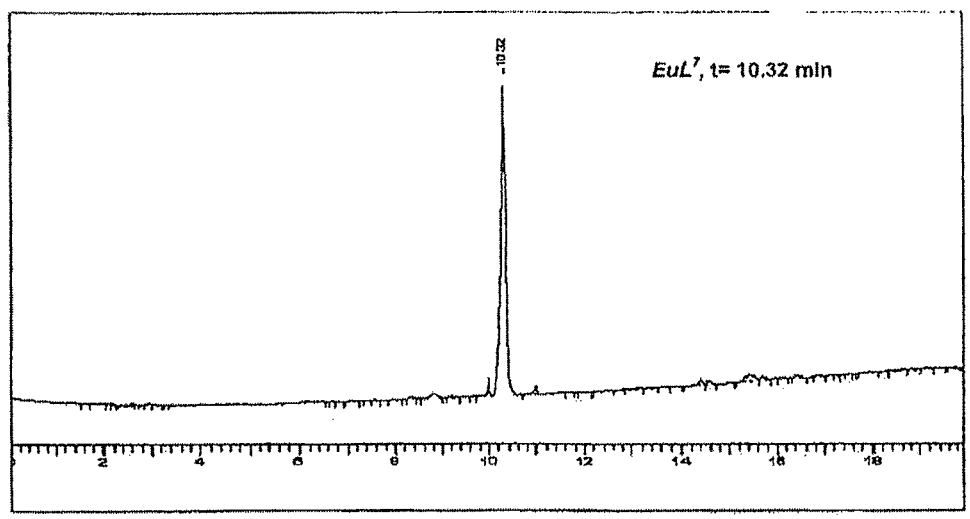
Figure 1H:
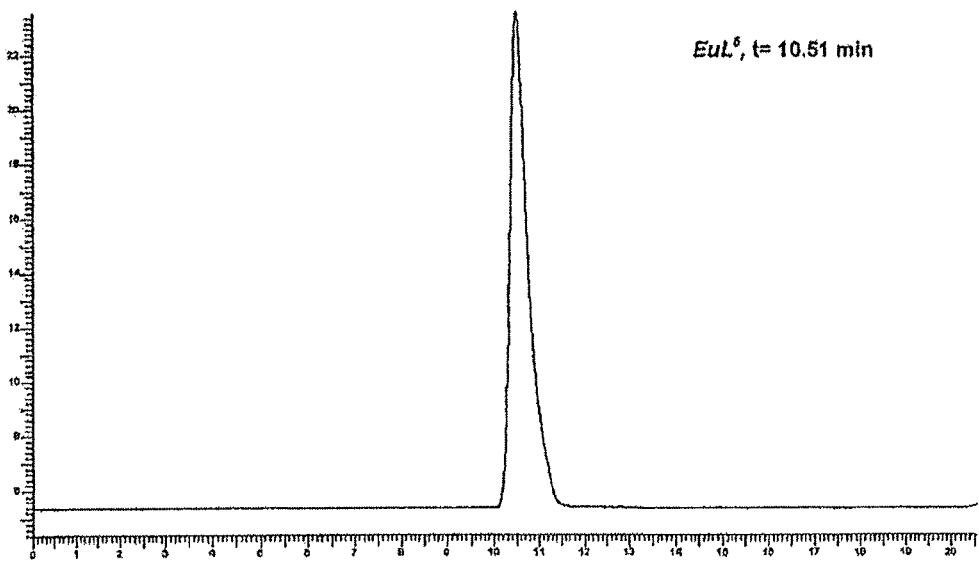
Figure 1I:
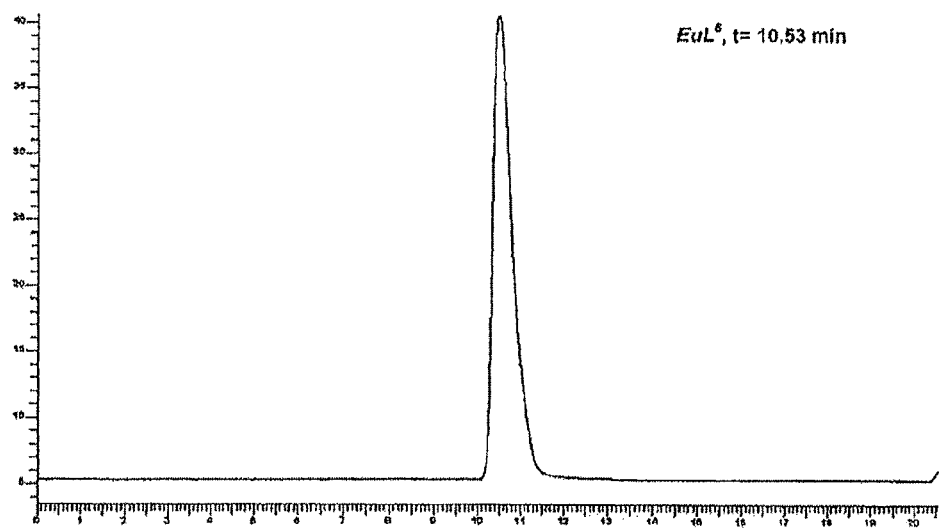

The present invention exploits the phenomenon of long-lived emission from lanthanide ions after excitation, luminescence that persists for several milliseconds and, in particular, the modulation of the lifetime and spectral form of the luminescence resultant from reversible displacement of co-ordinated water molecules or other more weakly bound molecules or anions. The anion binds reversibly in aqueous media to the lanthanide centre, altering the local coordination environment, leading to changes in emission spectral form, for example altering the relative intensity of several emission bands (see e.g. R. S. Dickins et al, *J. Am. Chem Soc.*, 2002, 124, 12697). By using time-gated spectral acquisition methods known to those of skill in the art, autofluorescence from samples of interest, luminescence from biomolecules found in such samples and undesired ligand fluorescence can be eliminated.

The compounds of formula (Ia) comprising azathiaxanthone moieties have been found to exhibit unexpectedly high selectivity for the citrate ion making use of chelation of the hydroxyl and α-carboxylate group by way of reversible displacement of coordinated water molecules. The compounds of formula (Ib) comprising azaxanthone moieties have been found to be selective towards binding of the lactate ion.

In the compounds of formula (Ia), R$^1$ is an optionally substituted 2-(1-azathiaxanthone) molecule, that is to say a 1-azaxanthone molecule attached to the remainder of the compound at its 2-position. In the compounds of formula (Ib), R$^1$ is an optionally substituted 2-(1-azaxanthone) molecule. Where substituted, substituents may be present, for example, at one or more of the 3, 7, 8 or 9 positions of the 1-aza(thia) xanthone moiety.

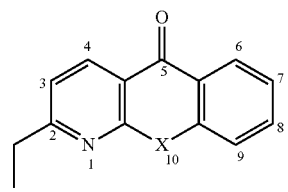

X = O or S (to remainder of compounds of formulae (I))

One or more substituents may be present on the two aromatic rings of the aza(thia)xanthone and these substituents may be, for example, independently selected from alkyl, acylamino, amido, carboxylate and ester substituents.

By alkyl is meant herein a saturated hydrocarbyl moiety that may comprise straight-chain, branched or cyclic regions. Typically an alkyl will comprise from 1 to 20 carbon atoms, more typically from 1 to 6 carbon atoms.

By aralkyl is meant herein an aryl or heteroaryl-substituted alkyl moiety. Typically the (hetero)aromatic moieties in aralkyl substituents are monocyclic, for example phenyl or monocyclic heteroaryl moieties such as pyridyl, furanyl, thiophenyl etc. Aryl or heteroaryl moieties may be substituted e.g. with one or more alkyl, alkyloxy (i.e. alkyl-O—), halo, nitro, amino, carboxy and ester substituents.

By acylamino is meant a substituent of formula —NH-COR, wherein R is this context is alkyl, aryl or heteroaryl and the hydrogen atom indicated is optionally replaced, but typically is not, with an alkyl, aryl or heteroaryl moiety. By amido is meant a substituent of formula —C(O)NH$_2$ in which one or both, typically one, of the hydrogen atoms indicated may be replaced with alkyl, aryl or heteraryl.

By carboxyl is meant a substituent of formula —CO$_2$H. A carboxyl substituent may, if desired, be derivatised to form esters of formula CO$_2$R, wherein R is this context is alkyl or aryl or heteroaryl, or amido substituents.

Often the 2-(1-aza(thia)xanthone) moiety will be unsubstituted or, if substituted, is substituent once or twice, e.g. once, with an alkyl, acylamino or carboxy, ester or amido substituent. A detailed description of how to access such derivatised 1-aza(thia)xanthone molecules is described by P. Atkinson et al. (*Org. Biomol. Chem.*, 2006, 4 1707-1722).

The R$^4$ substituents in compounds of formula (Ia) may be selected independently, but are typically the same, and comprise an amino acid or salt thereof, attached to the remainder of R$^2$ through the nitrogen atom of the amino group.

By amino acid is meant herein a molecule that comprises both an amino and a carboxylic acid functionality. Typically the amino acids employed according to this invention are, but need not be, naturally occurring amino acids comprising amino acid and carboxylic acids attached to a common carbon atom (the so-called α-carbon atom). As is known amino acids (natural or otherwise) may comprise additional amino or carboxylic acid moieties because of which the amino and carboxylic acid functionalities attached to the α-carbon atom are referred to as the α-amino and α-carboxylic acid groups. Typically $R^4$ is an amino acid, or salt thereof, (in particular a carboxylate salt, in which the carboxylic acid of the carboxyl group is deprotonated) attached to the remainder of $R^2$ through the nitrogen atom of the α-amino group.

The $R^4$ moieties, typically, are conveniently obtained from naturally occurring amino acids, for example phenylalanine or alanine (wherein —$R^4$ moieties are —N(H)C(H)(CH$_2$Ph)COOH (or a salt thereof) and —N(H)C(H)(CH$_3$)COOH (or a salt thereof) respectively). Other amino acids (including naturally occurring amino acids) are known to those skilled in the art. Examples of naturally occurring amino acids include alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine.

As a consequence of $R^4$ being attached to the remainder of $R^2$ through an amino group (typically via the α-nitrogen atom) the (or a) carboxylic acid of the amino acid group $R^4$ remains unreacted. As a consequence, the carboxylic acid is susceptible to derivatisation. Accordingly, the compounds of this invention of formula (Ia) may comprise the carboxylic acid of the amino acid as the free acid, or as the salt of the free acid, for example as a sodium, potassium or other convenient salt. In the complexes of the invention, the lanthanide ion may serve as the counterpart cation to the anionic carboxylate moieties, where the carboxylic acids of $R^4$ are deprotonated (as they are when present in salts of the free acids).

A particularly surprising feature of the present invention in relation to the compounds of formula (Ia), and complexes comprising these compounds, is the elevation of the apparent stability of ternary complexes of cationic lanthanide-containing complexes with citrate wherein the carboxylic acid moiety present in the $R^4$ substituents is esterified, (whereby to provide compounds not of the invention) in the presence of certain concentrations of divalent metals such as magnesium, zinc and calcium. Surprisingly, it has been found that carboxylate complexes in which the carboxylic moiety is not esterified (complexes of the invention) constitute complexes in which the stabilities of the ternary complexes are not elevated to such an extent. Furthermore, use of unesterified complexes gives rise to affinity and selectivity profiles that are particularly useful for the analysis of typical concentrations of citrate (for example over the range of 0.1 to 2 mM, after sample dilution by ×100) found in typical samples of interest (such as clinical samples). Notably, complexes analogous to those of the present invention in which the carboxylic acid groups of the $R^4$ moieties are esterified have been surprisingly found to possess too high a binding affinity to allow modulation of the emission spectral response over the target working range of citrate concentrations found in typical citrate-containing samples of interest. The foregoing is manifested in the data presented below (see Table 1), where the apparent affinity constant of a comparative example of the invention, comprising esterified $R^4$ substituents, increases by about two log units is the presence of 2 mM MCl$_2$ (M=Ca, Zn and Mg).

Finally, in the compounds of formula (Ia), substituent $R^3$ may be either hydrogen or a $C_{1-6}$ alkyl group. Where the $R^3$ substituent is other than hydrogen, the alkyl group may be, for example, a straight-chain or branched alkyl group, and in particular a straight-chain or branched $C_{1-4}$ straight chain or branched alkyl group such as a methyl, ethyl, n-propyl or iso-propyl or tert-butyl group. In certain embodiments of the invention $R^3$ in compounds of formula (Ia) is a methyl group. Such alkylated compounds may be prepared by Eschweiler-Clarke reaction of the parent secondary amine, exemplification of which is provided hereinafter. Typically, however, $R^3$ is hydrogen in compounds of formula (Ia) or complexes derived therefrom.

Figure 7:
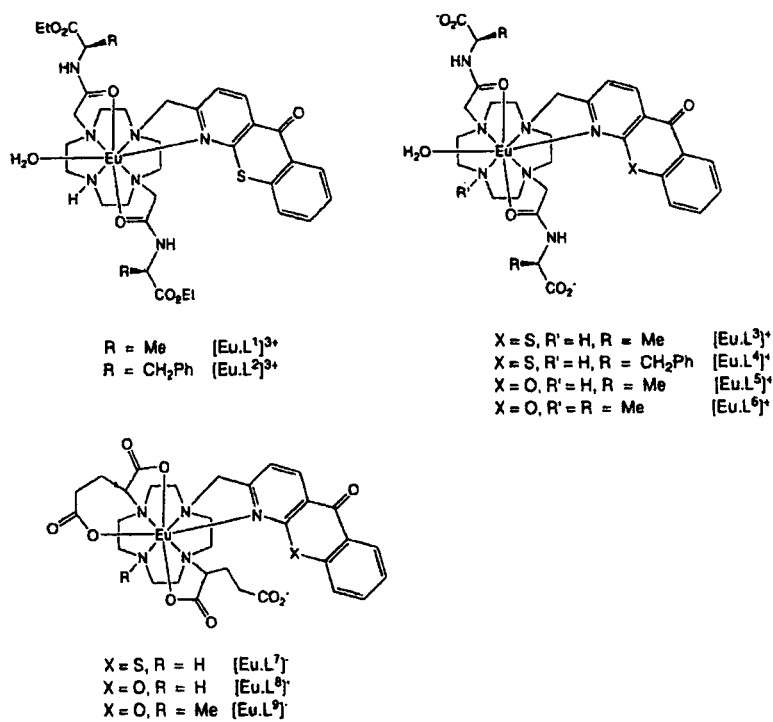
FIG. 7 shows some structures of europium (III) complexes of the invention and comparative complexes.

Examples of compounds of the invention of formula (Ia) in which the compounds are incorporated into lanthanide (III)-(e.g. Eu (III)-) containing complexes are depicted in FIG. 7 (ligands $L^3$ and $L^4$). Examples of compounds of the invention of formula (Ia) as thus of either of the following formulae:

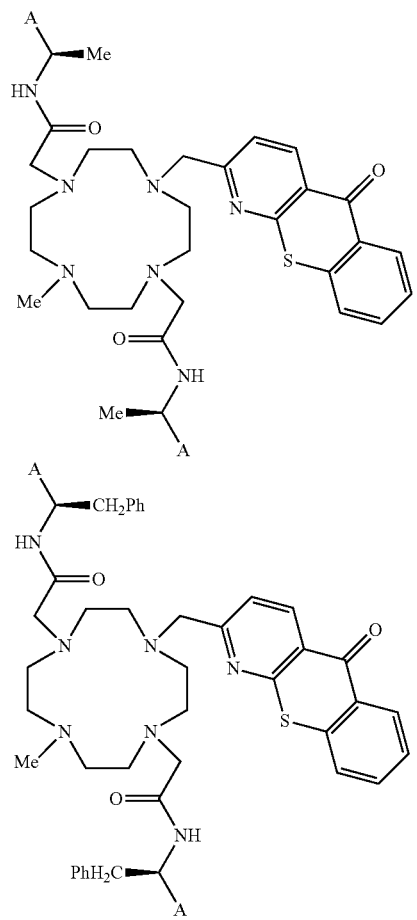

(wherein each -A is —CO$_2$H, or a salt thereof).

In the compounds of formula (Ib), $R^1$ is an optionally substituted 2-(1-azaxanthone) molecule as already described in detail hereinabove.

In compounds of formula (Ib), each $R^2$ is independently an optionally substituted glutaric or succinic acid, or a salt or ester thereof. Typically, both $R^2$ substituents will be the same. As is known by those with knowledge of the art, glutaric acid is a 5-carbon atom-containing dicarboxylic acid with the disposition of the carboxylic acids being at either end of a linear, saturated and unsubstituted hydrocarbyl chain. Succinic acid is an analogue of glutaric acid containing one less methylene group in the linear saturated, hydrocarbyl chain.

The position at which the glutaric or succinic acid is connected to the nitrogen atom in the compounds of formula (Ib) is typically at a carbon atom to which a carboxylic acid is connected, i.e. as a so-called α-carbon atom. With succinic acid, therefore, this typical point of connectivity is at either of the two carbon atoms to which the terminal carboxylic acids are connected; in glutaric acid, the point of connectivity is thus typically at a carbon atom other than the central carbon atom of the three carbon atom-containing chain linking the terminal carboxylic functionalities. The glutaric or succinic acids that may be employed in the compounds of formula (Ia) are typically unsubstituted, although a degree of substitution may be tolerated, with, for example, one or more halo, nitro, amino, hydroxyl or $C_{1-6}$ alkyl or $C_{2-6}$ alkenyl or alkynyl substitutents present.

Typically, the compounds of the invention of formula (Ib) comprise glutaric acid (i.e. unsubstituted glutaric acid) as each $R^2$, or a salt or ester thereof. Examples of compounds of the invention of formula (Ib) in which the compounds are incorporated into lanthanide (III)- (e.g. Eu (III)-) containing complexes are depicted in FIG. 7 (ligands and $L^8$ and $L^9$). Examples of compounds of the invention are thus of the following formula:

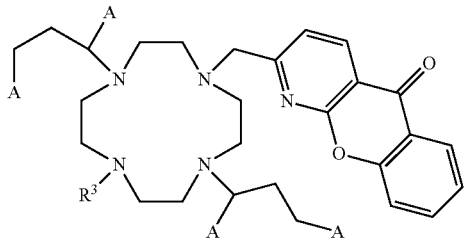

(wherein each -A is —$CO_2H$, or a salt thereof; and $R^3$ is either hydrogen or methyl). As will be understood by those skilled in the art, the carboxylic acid functionalities present in the glutaric or succinic acids of moieties $R^2$ may be present as the free acids, as salts, for example sodium or potassium salts, or esters, for example $C_{1-6}$ alkyl esters such as methyl or ethyl esters. Advantageously, where the macrocyclic compounds of formula (Ib) are part of a lanthanide-containing macrocyclic complex, the carboxylic acid functionalities are present in deprotonated form (i.e. as salts). In this way, each dicarboxylic acid substituent $R^2$ gives rise to the coordination to the lanthanide ion of the α-carboxylate (i.e. the carboxylate attached to the carbon atom attached to the nitrogen atom present in the compounds of formula (Ib) to which the substituents $R^2$ are connected) and one non α-carboxylic acid. In addition, one of the other carboxylic groups in one of the $R^2$ ligands may bind to the lanthanide ion in the complex. Competitive displacement of this non-α-carboxylate by binding with lactate in particular can occur and changes the coordination environment the lanthanide centre, this change to the coordination environment giving rise to the detectable modulation in emissivity of radiation upon excitation of the resultant lanthanide complex.

Finally, in the compounds of formula (Ib), substituent $R^3$ may be either hydrogen or a $C_{1-6}$ alkyl group. Where the $R^3$ substituent is other than hydrogen, as is often advantageous (but not necessary) with compounds of formula (Ib), the alkyl group may be, for example, a straight-chain or branched alkyl group, and in particular a straight-chain or branched $C_{1-4}$ straight chain or branched alkyl group such as a methyl, ethyl, n-propyl or iso-propyl or tent-butyl group. In certain embodiments of the invention $R^3$ in compounds of formula (Ib) is a methyl group. Such alkylated compounds may be prepared by Eschweiler-Clarke reaction of the parent secondary amine, exemplification of which is provided hereinafter. Advantageously, lanthanide-containing complexes comprising compounds of formula (Ib), wherein $R^3$ is a $C_{1-6}$ alkyl group, such as those described immediately hereinbefore, are less hydrated in solution and have increased steric demand at the lanthanide ion.

It will be understood by those skilled in the art that some of the compounds and complexes of the invention can exist in the form of one or more stereoisomers. Individual of mixtures of stereoisomers are embraced by the references herein to the compounds and complexes of the invention.

Exemplary compounds of the invention, which are described in the examples which follow below are 1,7-bis(α-dimethylglutarate)-4-[(1-azaxanthone)-2-methyl]-1,4,7,10-tetraaza-cyclododecane, 1,7-bis(α-glutarate)-4-[(1-azaxanthone)-2-methyl]-1,4,7,10-tetraaza-cyclododecane, 1,7-bis(α-dimethyl glutarate)-4-[(1-azaxanthone)-2-methyl]-10-methyl-1,4,7,10-tetraaza-cyclododecane, 1,7-bis(α-glutarate)-4-[(1-azaxanthone)-2-methyl]-10-methyl-1,4,7,10-tetraaza-cyclododecane, (SS)-1,7-bis(carboxy-2-ethylcarbamoylmethyl)-4-[(1-azathiaxanthone)-2-methyl]-1,4,7,10-tetraazacyclododecane and (SS)-1,7-Bis(carboxy-2-ethylcarbamoylphenyl)-4-[(1-azathiaxanthone)-2-methyl]-1,4,7,10-tetraazacyclododecane.

As described above, the compounds of formula (I) of this invention may be used to provide luminescent lanthanide complexes by binding to a lanthanide ion, in particular a lanthanide (III) ion. The lanthanide ion may be selected from the following: Ln(III), Ln=Nd, Sm, Eu, Gd, Tb, Dy, Ho, Er, Tm, Yb and is typically Eu(III) or (Tb(III), in particularly Eu(III). In the complexes of the invention in which the compounds of formula (I) are complexed with a lanthanide ion, the direct coordination of the chromophore (i.e. either an azathiaxanthone or azaxanthone) to the central lanthanide ion minimises the separation between the azathiaxanthone or azaxanthone sensitiser and the acceptor lanthanide ion ensuring efficient energy transfer and efficient luminescence.

The resultant complexes are particularly effective in the selective analysis, i.e. detection and/or quantification, in samples of interest, typically obtained from living beings, in particular a mammal, most particularly a human, in order to analyse for citrate or lactate. Such samples may be of blood, plasma, serum, urine, saliva, mucus, perspiration, lymph, gastric juice, aqueous humour, semen or prostatic fluid. Such samples may be amniotic, pericardial, peritoneal, pleural, cerebrospinal, vaginal or faecal. Typically samples are of serum, urine, saliva, seminal or prostate fluid samples. Where such samples, typically liquid samples, are obtained from a human or an animal body, it will be appreciated that the actual in vivo obtaining of a (liquid) sample from such a human or animal body is not an essential part of the methods of the invention described herein. In particular, the obtaining of a liquid sample can take place before practice of, and so be omitted from, the methods according to the fifth to ninth aspects of the present invention such that the liquid sample, or sample of interest (also typically a liquid sample) may be defined as having been previously obtained from a living being. Alternatively the methods according to the fifth to ninth aspects of the invention may specifically not be a diagnostic method practised on the human or animal body.

In this way the methods according to the seventh to ninth aspects of the present invention may be, or be part of, an in vitro diagnostic method.

Excitation of lanthanide (III) complexes of the invention in solution with wavelengths in the range 335-405 (±20) nm afford metal-based emission spectra with emission bands from about 580 to about 700 nm. As is known (P. Atkinson et al., *Org. Biomol. Chem.*, 2006, 4, 1707) coordination of the pyridyl nitrogen atom of aza(thia)xanthones to lanthanide (III) ions permits efficient sensitisation of lanthanide emission with the $\lambda_{exc}$ varying with the particular aza(thia)xanthone employed. For example complexes comprising compounds of formula (Ia) are appropriately excited with radiation of about 336 or 337 (±20) nm; complexes comprising compounds of formula (Ib) are appropriately excited with radiation of about 380 (±25) nm. In each case, the most appropriate excitation energy can be selected by the skilled person, by reference to the resultant emission spectrum.

Preparatory to practising the various methods of this invention, a calibration curve may be established in order to allow correlation between emission bands with known quantities of citrate and lactate in a relevant calibration sample. Such preparatory methods allow appropriate working ranges for the analysis to be defined.

For example, as described in greater detail below, a simulated prostate fluid background containing 0.3 M HSA, 0.1 NaCl, 4 mM KCl, 3 mM NaHCO$_3$, 4 mM CaCl$_2$, 2 mM ZnCl$_2$, 5 mM MgCl$_2$ (pH 6.5, 0.1 M HEPES) allows modulation of europium emission at 10 μM concentration) with lactate concentrations in the range 0 to 1 mM.

It may be desirable to dilute liquid samples obtained clinically, e.g. seminal or prostatic fluid samples) prior to practice of the methods of this invention in order that typical lactate or citrate concentrations found in clinical sample can be diluted into the working concentrations of the analysis. Appropriate dilution protocols can be established easily by those skilled in the art. For example, a 1 μL as a sample of fluid (e.g. seminal or prostate) may be conveniently diluted by a factor of 100 allowing analysis in a 50 μL optical cuvette.

Also preparatory to practice of the various methods of this invention may be filtration of the samples obtained initially (e.g. clinically), for example to remove large biomolecules such as proteins or polysaccharides, which might otherwise interfere with the analysis. This may easily be achieved by filtration, for example, through a 10 kD cut-off filter. Using these methods, as is described in greater detail in the experimental section, lactate samples in urine (3.5 simple mM), seminal fluid (3.8 mM), prostate fluid (4 mM) and reconstituted human serum (1.9 mM) were found to be within 10% of the concentration determined enzymatically. In saliva, each method (enzymatic and of the invention) gave a zero reading for lactate (±) 0.2 mM).

Analogously, preparatory methods (including dilution and filtration) can be undertaken in connection with the analysis of citrate. Typically, prostatic fluids are diluted by a factor of about 100 prior to analysis. According to the methods of the invention as described in greater detail hereinbelow, citrate concentrations ranging from 12 mM to 160 mM in 14 samples of prostate fluid were measured and confirmed to be within 10% of the concentrations deduced using a citrate lyase enzyme kit (for which the amount of bio-fluid required was notably 25 times greater). Using similar methods, but with a 10-fold dilution, citrate could be determined in the urine of healthy volunteers between a range of from 3.5-5.5 mM (±10%).

In accordance with the methods of this invention, after a contact of a sample of interest with a complex of the present invention, and optionally the preparatory steps described herein, analysis for the presence of citrate or lactate may be achieved by analysis of the spectrum of luminescent radiation emitted upon excitation for any modulation resultant from contact with the sample of interest. Whilst it will be appreciated that the modulation in intensity of any given emission band within the emission spectrum may be measured to report upon the quantity or concentration of the analyte under analysis, the principle of ratiometric detection, in which changes in the ratio emissivities at two different wavelengths are compared, as is known to those in the art, imparts a greater precision to the analysis. In particular, ratiometric assays typically allow a 3% variance in the measured intensity ratio for a given concentration of analyte (citrate or lactate).

As described below, ratiometric detection of citrate in samples of interest may be achieved by monitoring ratios between up to six different emission wavelengths as a function of citric acid concentration. With a complex of the present invention of formula (Ia), the intensity ratios of the 613/586 or 614/683 nm emission bands may be measured (although it is again stressed that it will be appreciated by those skilled in the art that the particular emission bands and their $\lambda_{max}$ will vary depending upon the particular complexes used).

In the analysis of lactate in samples of interest using a complex of the invention, as described below, ratiometric detection may be achieved by plotting changes in the ratio of up to 4 different wavelengths. In this way, the intensity ratio of the 692/619, 613/622, or 613/619 nm emission bands may be measured against change in lactate concentration whereby to establish a calibration curve.

Thus, it will be appreciated that, by using known quantities of citrate or lactate, it is possible to construct calibration curves that may be used to determine the presence, and if so the quantity or concentration, of citrate or lactate present in samples of interest. It will also be appreciated that dilution of the sample of interest may be necessary or advantageous prior to contact with the complex of the invention in accordance with the working range of detection established from construction of the calibration curve. The construction of appropriate calibration curves, working ranges for citrate and lactate concentrations and appropriate dilution (or concentration) modifications are well within the abilities of those skilled in the art.

The use of time-gated measurements may be used to eliminate any interference from concomitant chromophore fluorescence, in particular in the analysis of citrate according to the methods of this invention.

It will immediately be understood by those skilled in the art how the methods of the invention may be used and are useful in the screening or diagnosis of the various medical conditions related to abnormal concentrations of citrate or lactate found in various bodily samples, in allowing a determination of the concentrations of these analyses in subjects. For example, the medical practitioner will be able to correlate the concentration of citrate, or lactate, found in samples of interest, e.g. of clinical origin, with typical concentrations found in healthy patients, or in patients susceptible to, or suffering from medical conditions such as prostate cancer, associated with excessive lactic acid (e.g. lactic acidosis, hyperlactemia) or renal abnormalities such as renal metabolic imbalance, nephrocalcinosis or nephrolithiasis.

In summary, the invention provides for a rapid luminescence measurement that allows the determination of citrate or lactate in low volume (<5 μL) samples of various biological fluids. The methods are rapid (<5 min.) and offer considerable promise as alternatives to classical enzymatic assays.

The mention of all patent of other publications referred to herein is to be understood as if each and every one of these publications had been specifically incorporated by reference in their entirety.

The invention is now illustrated by the following non-limiting examples:

Example 1

Synthesis of [Eu.L$^8$]

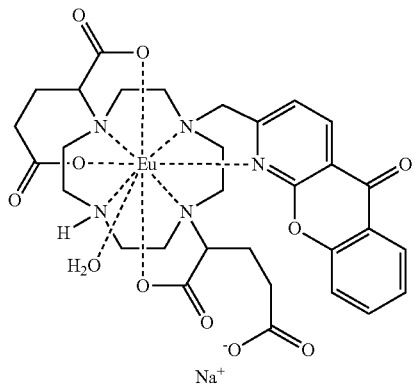

1,7-Bis(α-dimthylglutarate)-4-[(1-azaxanthone)-2-methyl]-1,4,7,10-tetraaza-cyclododecane

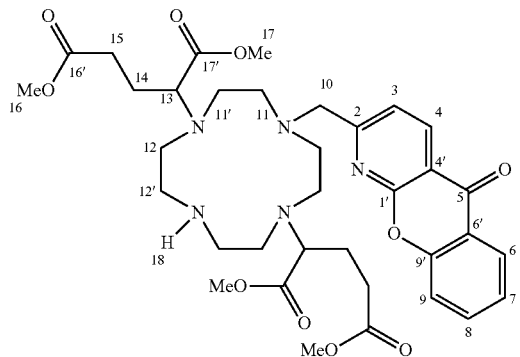 [SMILES: COC(=O)CCC(C(=O)OC)N1CCNCCN(C(CCC(=O)OC)C(=O)OC)CCN(Cc2ccc3c(=O)c4ccccc4oc3n2)CC1]

1,7-Bis(α-dimethylglutarate)-1,4,7,10-tetraazacyclododecane (130 mg, 266 μmol) was combined with 2-bromomethyl-1-azaaxanthone (1 eq., 80 mg) and NaHCO$_3$ (1.1 eq., 24 mg) and the mixture stirred in dry MeCN (4 mL) at 55° C. under argon for 48 h. The reaction was monitored by TLC (DCM:MeOH, 96:4) and ESMS$^+$ to confirm that the brominated starting material had been consumed. The solvent was removed under reduced pressure and the resulting solid was dissolved in a small volume of DCM (5 mL) and the sodium salts flitered off. The crude mixture was purified by column chromatography (DCM→0.2% MeOH) to yield the title compound as a yellow oil (82 mg, 118 μmol, 44%); δ$_H$ (CDCl$_3$) 8.64 (1H, d, J 8.0 Hz, H$^4$), 8.27 (1H, d, J 8.0 Hz, H$^6$), 7.89 (1H, d, J 8.0 Hz, H$^9$), 7.78 (1H, t, J 8.0 Hz, H$^8$), 7.40 (1H, t, J 8.0 Hz, H$^7$), 7.31 (1H, d, J 8.0 Hz, H$^3$), 3.88 (2H, s, H$^{10}$), 3.67 (6H, s, H$^{16}$), 3.57 (6H, s, H$^{17}$), 3.35 (2H, t, H$^{13}$), 3.00 (16H, m, H$^{11,11',12,12'}$), 2.36 (4H, m, H$^{15}$), 1.93 (4H, m, H$^{14}$); δ$_C$ (CDCl$_3$) 177.6 (C$^5$) 173.3 (C$^{16'}$), 172.6 (C$^{17'}$), 162.9 (C$^2$), 160.3 (C$^{4'}$), 155.9 (C$^{6'}$), 138.1 (C$^4$), 136.1 (C$^8$), 126.7 (C$^6$), 125.0 (C$^7$), 121.7 (C$^{1'}$), 121.3 (C$^3$), 119.3 (C$^9$), 115.9 (C$^{9'}$), 65.5 (C$^{13}$), 53.7 (C$^{10}$), 51.9 (C$^{16,17}$), 51.4, 50.8, 48.9, 46.7 (C$^{11,11',12,12'}$), 30.8 (C$^{15}$), 25.7 (C$^{14}$); R$_f$ 0.38 (DCM—4% MeOH, alumina); m/z (HRMS$^+$) 698.3403 (M+H)$^+$ (C$_{35}$H$_{48}$O$_{10}$N$_5$ requires 689.3396).

1,7-Bis(α-glutarate)-4-[(1-azaxanthone)-2-methyl]-1,4,7,10-tetraaza-cyclododecane

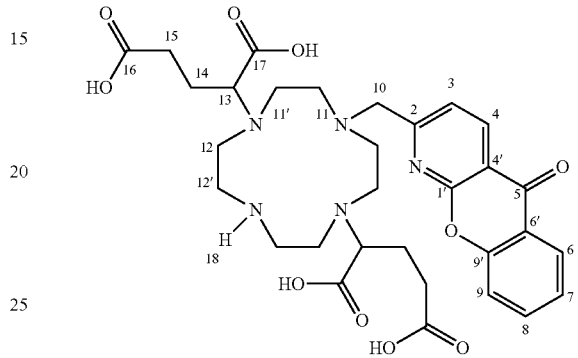

Freshly made aqueous KOD solution (3 mL, 0.1 M) was added to 1,7-bis(α-dimethylglutarate)-4-[(1-azaxanthone)-2-methyl]-1,4,7,10-tetraaza-cyclododecane (42 mg, 61 μmol). The reaction mixture was kept under argon at room temperature and progress was monitored by NMR. After 6 h no methyl ester signals were observed in the $^1$H-NMR spectrum. The pH of the mixture was decreased (pH≈6) with conc. HCl and the solution loaded onto a DOWEX 50X4-100 strong cation exchange resin. The column was eluted with water→10% NH$_4$OH and the fractions were analysed by $^{1H}$-NMR. The fractions were combined and lyophilised to yield the title compound as a pale yellow glass (15 mg, 23.5 μmol, 39%), which was used in a complexation reaction immediately. δ$_H$ (D$_2$O) 8.56 (1H, d, J 8.0 Hz, H$^4$), 8.02 (1H, d, J 8.0 Hz, H$^6$), 7.78 (1H, d, J 8.0 Hz, H$^9$), 7.41 (3H, br.m, H$^{8,3,7}$), 3.53 (2H, s, H$^{10}$), 3.09 (18H, br.m, H$^{11,11',12,12',13}$), 2.11 (8H, br.m, H$^{14,15}$); m/z (ESMS$^-$) 637 (M−H)$^-$.

[NaEuL$^8$]

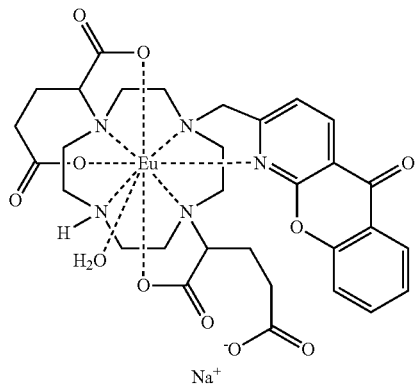

1,7-Bis(α-glutarate)-4-[(1-azathiaxanthone)-2-methyl]-1,4,7,10-tetraaza-cyclododecane (15 mg, 23.5 µmol) was added to Eu(CH$_3$CO$_2$)$_3$.3H$_2$O (1.1 eq., 10 mg) and the solids dissolved in aqueous methanol (10:1, 3 mL). The pH was carefully adjusted to 5.5 by addition of acetic acid and the reaction left to stir at 70° C. for 48 hrs. After the reaction was cooled to room temperature, the solvents were removed under reduced pressure and the remaining residue was dissolved in H$_2$O (3 mL). The pH was adjusted carefully to 10 by addition of conc. aqueous NaOH solution (in order to remove any excess Eu$^{3+}$ as Eu(OH)$_3$) resulting in a white precipitate that was removed via centrifugation. The pH was adjusted back to neutral with acetic acid and the mixture lyophilised to give a bright yellow solid contained about 2% NaOAc as a result of pH adjustment (14 mg, 20 µmol). m/z (HRMS$^-$) 791.1646 (M−H)$^-$ (C$_{31}$H$_{35}$O$_{10}$N$_5$$^{151}$Eu requires 791.1635); $\lambda_{max}$ (H$_2$O) 336 (5010 dm$^3$mol$^{-1}$cm$^{-1}$); $\tau^{Eu}_{(H2O, pH=3.0)}$: 0.37 ms, $\tau^{Eu}_{(H2O, pH=8.0)}$: 0.41 ms; $\tau^{Eu}_{(D2O, pD=2.6)}$: 0.93 ms, $\tau^{Eu}_{(D2O, pD=8.6)}$: 0.98 ms; $\phi^{Eu}_{(pH=3.0)}$=8%, $\phi^{Eu}_{(pH=8.0)}$=5%.

Example 2

Synthesis of [Eu.L$^9$]

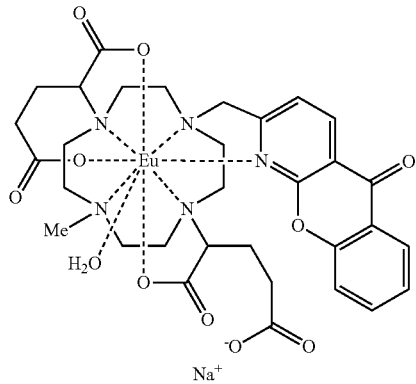

1,7-Bis(α-dimethylglutarate)-4-[(1-azaxanthone)-2-methyl]-10-methyl-1,4,7,10-tetraaza-cyclododecane

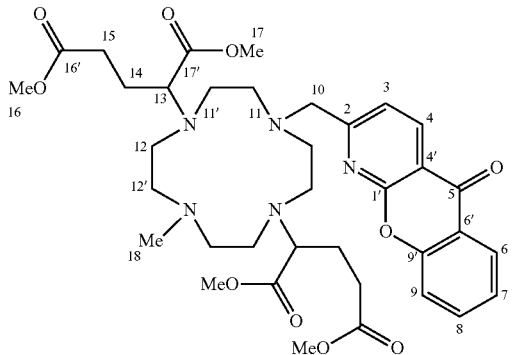 [SMILES: COC(=O)CCC(C(=O)OC)N1CCN(C)CCN(C(CCC(=O)OC)C(=O)OC)CCN(Cc2ccc3c(=O)c4ccccc4oc3n2)CC1]

1,7-Bis(α-dimethylglutarate)-4-[(1-azaxanthone)-2-methyl]-1,4,7,10-tetraaza-cyclododecane (40 mg, 58 µmol) was added to a solution of formic acid (1 mL) and aqueous formaldehyde (38%, 1 mL) and the mixture was boiled under reflux for 48 h. After filtration and removal of the solvent, the residue was treated with aqueous sodium hydroxide solution (2 M, 5 mL) and extracted with chloroform (3×10 mL). The combined extracts were dried and the solvent was removed under reduced pressure to yield a bright yellow solid (40 mg, 56 µmol, 97%); δ$_H$ (CDCl$_3$) 8.64 (1H, d, J 8.0 Hz, H$^4$), 8.25 (1H, d, J 8.0 Hz, H$^6$), 7.86 (1H, m, H$^9$), 7.79 (1H, t, J 8.0 Hz, H$^8$), 7.34 (2H, m, J 8.0 Hz, H$^{3,7}$), 3.88 (2H, s, H$^{10}$), 3.67 (6H, s, H$^{16}$), 3.57 (6H, s, H$^{17}$), 3.35 (2H, t, H$^{13}$), 3.00 (21H, m, H$^{11,11',12,12',18}$ $_{(dist. s\ at\ 2.94)}$), 2.34 (4H, m, H$^{15}$), 1.90 (4H, m, H$^{14}$); m/z (HRMS$^+$) 712.3564 (M+H)$^+$ (C$_{36}$H$_{50}$O$_{10}$N$_5$ requires 712.3552).

1,7-Bis(α-glutarate)-4-[(1-azaxanthone)-2-methyl]-10-methyl-1,4,7,10-tetraaza-cyclododecane

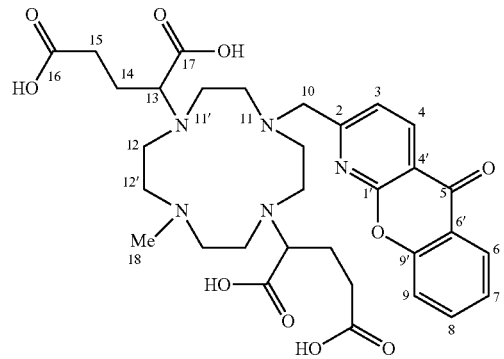 [SMILES: CN1CCN(C(CCC(=O)O)C(=O)O)CCN(Cc2ccc3c(=O)c4ccccc4oc3n2)CCN(C(CCC(=O)O)C(=O)O)CC1]

Freshly made aqueous KOD solution (2.5 mL, 0.1 M) was added to 1,7-bis(α-dimethylglutarate)-4-[(1-azathiaxanthone)-2-methyl]-10-methyl-1,4,7,10-tetraaza-cyclododecane (40 mg, 56 µmol). The reaction mixture was kept under argon at room temperature and progress was monitored by NMR. After 4 h no methyl ester resonances were observed in the $^1$H-NMR spectrum. The pH of the mixture was decreased (pH≈6) with conc. HCl and the solution loaded onto a DOWEX 50X4-100 strong cation exchange resin. The column was eluted with water→10% NH$_4$OH and the fractions were analysed by 1H-NMR. The fractions were combined and lyophilised to yield the title compound as a bright yellow powder (22 mg, 34 µmol, 61%), which was used in a complexation reaction immediately. δ$_H$ (D$_2$O): mainly broad overlapping signals; no Me groups in $^1$H-NMR, δ$_H$ (D$_2$O) 8.74 (1H, d, J 8.0 Hz, H$^4$), 8.17 (1H, d, J 8.0 Hz, H$^6$), 7.90 (2H, br.m, H$^{8,9}$), 7.57 (2H, br.m, J 8.0 Hz, H$^{3,7}$), 3.80 (2H, s, H$^{10}$), 3.27 (2H, t, H$^{13}$), 2.96 (21H, br.m, H$^{11,11',12,12',18}$ $_{(dist. s\ at\ 2.86)}$), 2.44 (4H, br.m, H$^{15}$), 1.97 (4H, br.m, H$^{14}$); m/z (ESMS$^-$) 651 (M−H)$^-$.

[NaEuL$^9$]

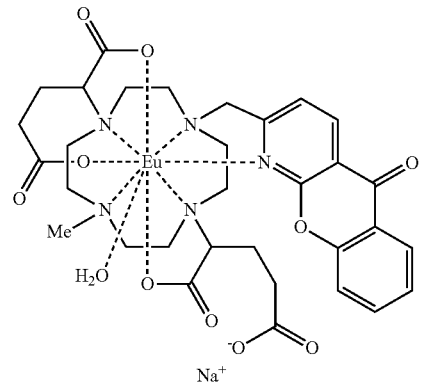

1,7-Bis(α-glutarate)-4-[(1-azathiaxanthone)-2-methyl]-10-methyl-1,4,7,10-tetraaza-cyclododecane (22 mg, 34 μmol) was added to Eu(CH$_3$CO$_2$)$_3$.3H$_2$O (1.1 eq., 15 mg) and the solids dissolved in aqueous methanol (10:1 mL). The pH was carefully adjusted to 5 by addition of acetic acid and the reaction left to stir at 55° C. for 30 h. After the reaction was cooled to room temperature, the solvents were removed under reduced pressure and the remaining residue was dissolved in H$_2$O (5 mL). The pH was then adjusted carefully to 10 by addition of conc. aqueous NaOH solution (in order to remove excess Eu$^{3+}$ as Eu(OH)$_3$) resulting in a white precipitate that was removed via centrifugation. The pH was adjusted back to neutral with acetic acid and the mixture lyophilised to give a bright yellow solid contained about 2% NaOAc as a result of pH adjustment (22 mg, 27 μmol). m/z (HRMS$^-$) 804.1759 (M−H)$^-$ (C$_{32}$H$_{38}$O$_{10}$N$_5$$^{151}$Eu requires 804.1758); $\lambda_{max}$ (H$_2$O) 336 (5010 dm$^3$mol$^{-1}$cm$^{-1}$); $\tau^{Eu}_{(H2O, pH=3.0)}$: 0.34 ms, $\tau^{Eu}_{(H2O, pH=8.0)}$: 0.77 ms; $\tau^{Eu}_{(D2O, pD=2.6)}$: 1.27 ms, $\tau^{Eu}_{(D2O, pD=7.6)}$: 1.26 ms; $\phi^{Eu}_{(pH=3.0)}$=26%, $\phi^{Eu}_{(pH=8.0)}$=11%

Example 3

Synthesis of [Eu.L$^5$] (Comparative Example)

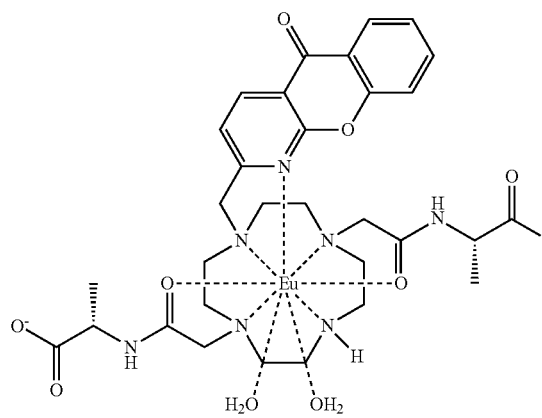

(SS)-1,7-Bis(ethoxycarbonyl-2-ethylcarbomoylmethyl)-4-[(1-azaxanthone)-2-methyl]-1,4,7,10-tetraazacyclododecane

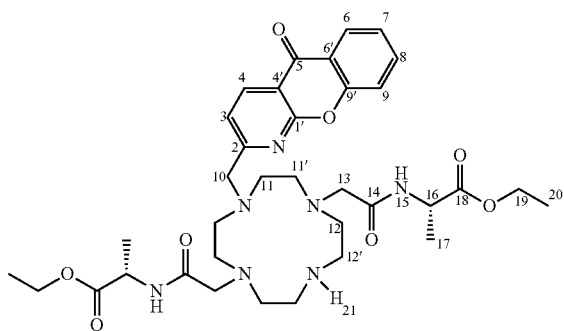 [SMILES: CCOC(=O)[C@H](C)NC(=O)CN1CCNCCN(CC(=O)N[C@@H](C)C(=O)OCC)CCN(Cc2ccc3c(=O)c4ccccc4oc3n2)CC1]

(SS)-1,7-Bis(ethoxycarbonyl-2-ethylcarbamoylmethyl)-1,4,7,10-tetraazacyclododecane (590 mg, 1.22 mmol) was combined with 2-bromomethyl-1-azaxanthone (1 eq., 350 mg) and NaHCO$_3$ (1 eq., 102 mg) and the mixture in dry MeCN (25 mL), was heated at 55° C. for 20 h under argon. The reaction was monitored by TLC (DCM, 3.5% MeOH, alumina) and ESMS$^+$ to confirm that the brominated starting material had been consumed. The solvent was removed under reduced pressure and the resulting solid was dissolved in a small volume of DCM (5 mL) and the potassium salts removed by filtration. The crude mixture was purified by column chromatography (DCM→3% MeOH, alumina); fractions containing clean product were combined and the solvents were removed under reduced pressure to yield the title compound as a pale yellow oil (300 mg, 432 μmol, 36%); $\delta_H$ (CDCl$_3$): 8.61 (H$^4$, d, 1H, J=8.0 Hz), 8.25 (H$^6$, dd, 1H, J=8.0 Hz), 7.76 (H$^8$, dt, 1H, J=8.0 Hz), 7.61 (H$^9$, d, 1H, J=8.0 Hz), 7.48 (H$^{15}$, br. s, 2H), 7.38 (H$^{3,7}$, m, 2H), 4.40 (H$^{16}$, 2H, p, J=7.0 Hz), 4.08 (H$^{19}$, q, 4H, J=7.0 Hz), 3.98 (H$^{10}$, s, 2H), 3.20 (H$^{11,11',12,12',13}$, m, 20H) 1.34 (H$^{17}$, d, 6H, J=7.0 Hz), 1.19 (H$^{20}$, t, 6H, J=7.0 Hz); $\delta_c$ (CDCl$_3$) 177.4 (C$^5$), 173.2 (C$^{18}$), 170.4 (C$^{14}$), 164.0 (C$^2$), 160.2 (C$^{1'}$), 155.8 (C$^9$), 138.1 (C$^4$), 136.0 (C$^8$), 126.9 (C$^6$), 125.1 (C$^7$), 121.8 (C$^{6'}$), 121.4 (C$^3$), 118.7 (C$^9$), 115.8 (C$^{4'}$), 61.5 (C$^{19}$), 60.3 (C$^{10}$), 56.2 (C$^{13}$), 54.1, 52.9, 51.4, 47.1 (C$^{11,11',12,12'}$), 47.1 (C$^{16}$), 17.9 (C$^{17}$), 14.3 (C$^{20}$), m/z (HRMS$^+$) 696.3712 (M+H)$^+$ (C$_{35}$H$_{50}$O$_8$N$_7$ requires 696.3715) R$_f$ 0.40 (alumina, DCM with 3.5% MeOH).

(SS)-1,7-Bis(carboxy-2-ethylcarbamoylmethyl)-4-[(1-azaxanthone)-2-methyl]-1,4,7,10-tetraazacyclododecane

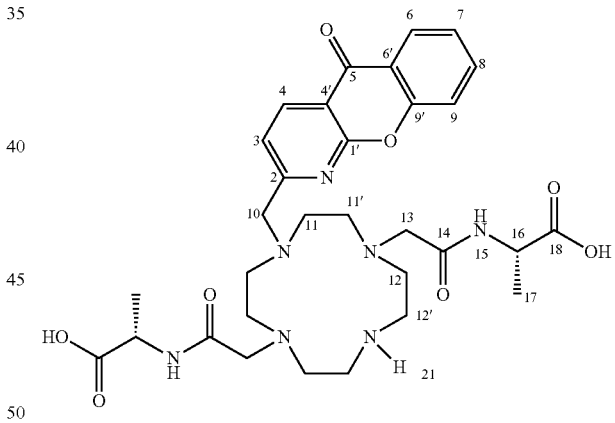

Freshly made aqueous KOD solution (5 mL, 0.1 M) was added to (SS)-1,7-bis(ethoxycarbonyl-2-ethylcarbamoylmethyl)-4-[(1-azaxanthone)-2-methyl]-1,4,7,10-tetraazacyclo-dodecane (85 mg, 122 μmol). The reaction mixture was kept under argon at room temperature and progress was monitored by NMR. After 6 h no ethyl group signals were observed in the $^1$H-NMR spectrum. The pH of the mixture was increased (pH≈6) with conc. HCl and the solution loaded onto a DOWEX 50X4-100 strong cation exchange resin. The column was eluted with water→10% NH$_4$OH and the fractions analysed by $^1$H-NMR. Selected fractions were combined and lyophilised to yield the title compound as a pale yellow oil (30 mg, 47 μmol, 39%), which was used for complexation reaction immediately. $\delta_H$ (D$_2$O): 8.23 (H$^4$, br.d, 1H, J=7.8 Hz), 7.83 (H$^6$, br.d, 1H, J=7.8 Hz), 7.66 (H$^8$, br.t, 1H, J=7.8 Hz), 7.25 (H$^{3,7,9}$, br.m, 3H, J=7.8 Hz), 4.08 (H$^{16}$, br.m, 2H), 3.09 (H$^{10}$, s, 2H), 3.02 (H$^{11,11',12,12',13}$, br.m, 22H), 0.87 (H$^{17}$, d, 6H, J=7.1 Hz)

[EuL$^5$]OAc

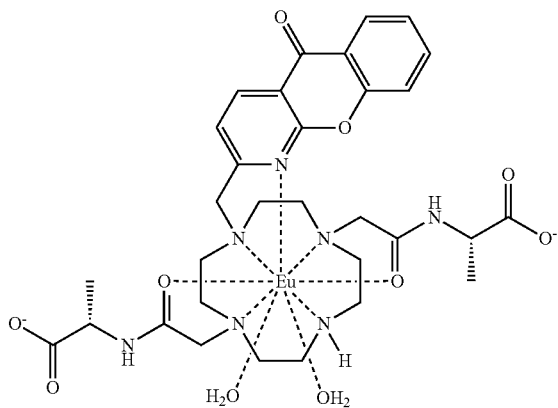

(SS)-1,7-Bis(carboxy-2-ethylcarbamoylmethyl)-4-[(1-azaxanthone)-2-methyl]-1,4,7,10-tetraazacyclododecane (30 mg, 47 μmol) was added to Eu(OAc)$_3$.4H$_2$O (1.1 eq., 19 mg) and the solids dissolved in aqueous methanol (10:1, 2.5 mL). The pH was carefully adjusted to 6 by addition of acetic acid and the reaction left to stir at 75° C. for 60 h. After the reaction was cooled to room temperature, the pH was adjusted carefully to 10 by addition of aqueous ammonia solution (35%) (in order to remove excess Eu as Eu(OH)$_3$) resulting in a white precipitate that was removed via centrifugation. The pH was adjusted back to neutral with acetic acid and the sample lyophilised to give a bright yellow solid (25 mg, 32 μmol, 68%). m/z (HRMS$^+$) 790.2121 (M+H) (C$_{31}$H$_{39}$O$_7$N$_7$Eu requires 790.2070); $\lambda_{max}$ (H$_2$O) 336 (5010 dm$^3$mol$^{-1}$cm$^{-1}$); $\tau^{Eu}_{(H_2O, pH=6.0)}$: 0.39 ms, $\tau^{Eu}_{(D_2O, pD=6.0)}$: 0.92 ms; $\phi^{Eu}_{(pH=6.0)}$=5%

Example 4

Synthesis of [Eu.L$^6$] (Comparative Example)

(SS)-1,7-Bis(ethoxycarbonyl-2-ethylcarbamoylmethyl)-4-[(1-azaxanthone)-2-methyl]-10-methyl-1,4,7,10-tetraazacyclododecane

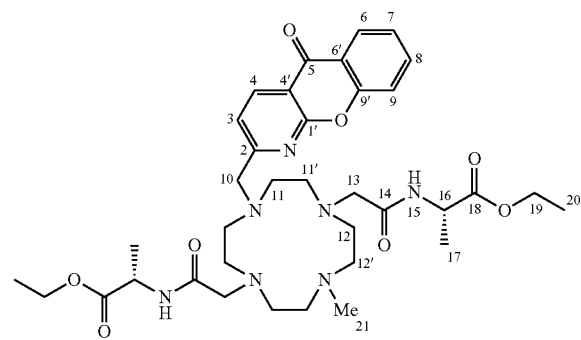 [SMILES: CCOC(=O)[C@H](C)NC(=O)CN1CCN(C)CCN(CC(=O)N[C@@H](C)C(=O)OCC)CCN(Cc2ccc3c(=O)c4ccccc4oc3n2)CC1]

(SS)-1,7-Bis(ethoxycarbonyl-2-ethylcarbamoylmethyl)-4-[(1-azaxanthone)-2-methyl]-1,4,7,10-tetraazacyclododecane (100 mg, 144 μmol) was added to a solution of formic acid (2 mL) and aqueous formaldehyde (38%, 2 mL) and the mixture was boiled under reflux for 20 h. After removal of the solvent under reduced pressure, the residue was treated with DCM:MeOH (10 mL, 10:1) and the paraformaldehyde by-product was removed via a combination of filtration and centrifugation. The organic solvent was removed under reduced pressure to yield the title compound as a bright yellow solid (84 mg, 118 μmol, 83%); δ$_H$ (CDCl$_3$): 8.63 (H$^4$, d, 1H, J=7.9 Hz), 8.23 (H$^6$, dd, 1H, J=7.9 Hz), 7.75 (H$^8$, dt, 1H, J=7.9 Hz), 7.54 (H$^{3,9}$, m, 2H, J=7.9 Hz), 7.38 (H$^7$, dt, 1H, J=7.9 Hz), 6.78 (H$^{15}$, br. s, 2H), 4.36 (H$^{16}$, 2H, p, J=7.0 Hz), 4.06 (H$^{10,19}$, m, 6H), 3.15 (H$^{11,11',12,12',13,21 \,(dist.\, s\, at\, 2.97)}$, m, 20H), 1.35 (H$^{17}$, d, 6H, J=7.0 Hz), 1.18 (H$^{20}$, t, 6H, J=7.0 Hz); δ$_c$ (CDCl$_3$) 177.3 (C$^5$), 172.8 (C$^{18}$), 170.8 (C$^{14}$), 165.2 (C$^2$), 160.1 (C$^{1'}$), 155.7 (C$^{9'}$), 138.6 (C$^4$), 136.1 (C$^8$), 126.9 (C$^6$), 125.2 (C$^7$), 121.8 (C$^{6'}$), 121.7 (C$^3$), 118.6 (C$^9$), 116.0 (C$^{4'}$), 61.5 (C$^{19}$), 60.6 (C$^{13}$), 56.0 (C$^{10}$), 53.8, 53.5, 49.9, 47.4 (C$^{11,11',12,12'}$), 48.5 (C$^{16}$), 43.7 (C$^{21}$), 17.3 (C$^{17}$), 14.3 (C$^{20}$), m/z (HRMS$^+$) 710.3870 (M+H)$^+$ (C$_{36}$H$_{52}$O$_8$N$_7$ requires 710.3857)

(SS)-1,7-Bis(carboxy-2-ethylcarbamoylmethyl)-4-[(1-azaxanthone)-2-methyl]-10-methyl-1,4,7,10-tetraazacyclododecane

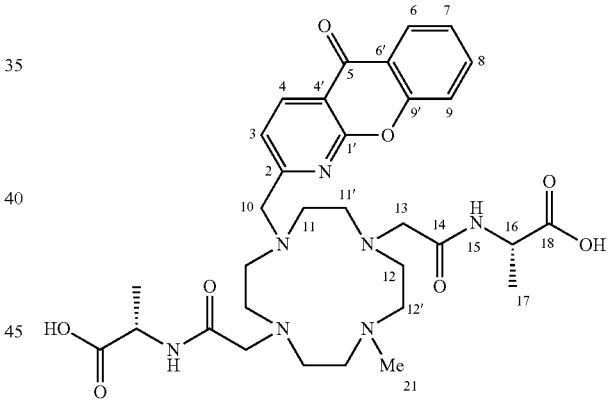

Freshly made aqueous KOD solution (5 mL, 0.1 M) was added to (SS)-1,7-bis(ethoxycarbonyl-2-ethylcarbamoylmethyl)-4-[(1-azaxanthone)-2-methyl]-10-methyl-1,4,7,10-tetraazacyclo-dodecane (84 mg, 118 μmol). The reaction mixture was kept under argon at room temperature and progress was monitored by NMR. After 6 h no ethyl group signals were observed in the $^1$H-NMR spectrum. The pH of the mixture was increased (pH 6) with conc. HCl and the solution loaded onto a DOWEX 50X4-100 strong cation exchange resin. The column was eluted with water→10% NH$_4$OH and the fractions were analysed by $^1$H-NMR. The fractions were combined and lyophilised to yield the title compound as a pale yellow oil (30 mg, 46 μmol, 39%), which was used in a complexation reaction immediately. δ$_H$ (D$_2$O): 8.18 (H$^4$, br.d, 1H, J=8.0 Hz), 7.74 (H$^{6,8}$, br.m, 2H, J=8.0 Hz), 7.21 (H$^{3,7,9}$, br.m, 3H, J=8.0 Hz), 3.84 (H$^{16}$, br.m, 2H), 3.15 (H$^{10}$, s, 2H), 3.02 (H$^{11,11',12,12',13,21 \,(dist.\, s\, at\, 2.78)}$, br.m, 25H), 1.05 (H$^{17}$, d, 6H, J=7.2 Hz)

23

[EuL⁶]OAc

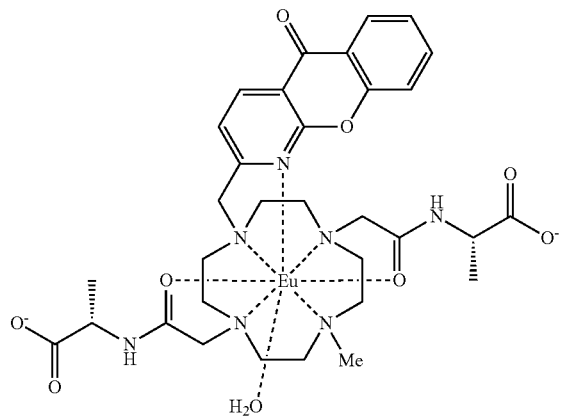

(SS)-1,7-Bis(carboxy-2-ethylcarbamoylmethyl)-4-[(1-azaxanthone)-2-methyl]-10-methyl 1,4,7,10-tetraazacyclododecane (30 mg, 47 μmol) was added to Eu(OAc)$_3$.4H$_2$O (1.1 eq., 19 mg) and the solids dissolved in 2.5 mL H$_2$O: MeOH (10:1). The pH was carefully adjusted to 6 by addition of acetic acid and the reaction left to stir at 75° C. for 60 h. After the reaction was cooled to room temperature, The pH was then adjusted carefully to 10 by addition of aqueous ammonia (35%) solution (in order to remove any excess Eu as Eu(OH)$_3$) resulting in a white precipitate that was removed via centrifugation. The pH was adjusted back to neutral with acetic acid and the sample lyophilised to give a bright yellow solid (23 mg, 29 μmol, 61%). m/z (HRMS⁺) 804.2232 (M+H) (C$_{32}$H$_{41}$O$_7$N$_7$Eu requires 804.2230); λ$_{max}$ (H$_2$O) 336 (5010 dm$^3$mol$^{-1}$cm$^{-1}$); τ$^{Eu}_{(H2O, pH=6.0)}$: 0.62 ms, τ$^{Eu}_{(D2O, pD=6.0)}$: 1.42 ms; φ$^{Eu}_{(pH=6.0)}$=5%.

Example 5

Synthesis of [Eu.L¹] (Comparative Example)

(SS)-1,7-Bis(ethoxycarbonyl-2ethylcarbamoylmethyl)-4-[(1-azathiaxanthone)-2-methyl]-1,4,7,10-tetraazacyclododecane

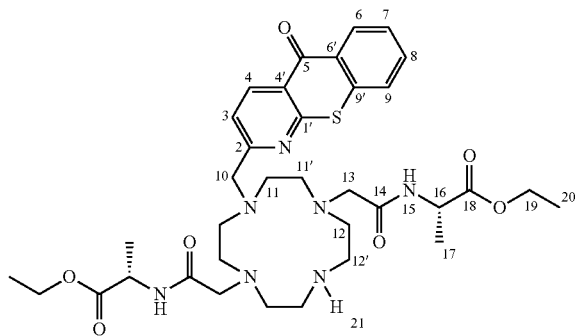 [SMILES: CCOC(=O)[C@H](C)NC(=O)CN1CCNCCN(CC(=O)N[C@@H](C)C(=O)OCC)CCN(Cc2ccc3c(=O)c4ccccc4sc3n2)CC1]

(SS)-1,7-Bis(ethoxycarbonyl-2-ethylcarbamoylmethyl)-1,4,7,10-tetraazacyclododecane (200 mg, 411 μmol) was combined with 2-bromomethyl-1-azathiaxanthone (1 eq., 126 mg) and KHCO$_3$ (1 eq., 41 mg) and the mixture stirred in dry MeCN (10 mL), was heated at 70° C. for 36 h under argon. The reaction was monitored by TLC (DCM, 5% MeOH, alumina) and ESMS⁺ to confirm that the brominated starting material had been consumed. The solvent was removed under reduced pressure and the resulting solid was dissolved in a small volume of DCM (5 mL) and the potassium salts removed by filtration. The crude mixture was purified by column chromatography (DCM→3% MeOH, alumina); fractions containing clean product were combined and the solvents were removed under reduced pressure to yield the title compound as a pale yellow oil (130 mg, 182 μmol, 45%); δ$_H$ (CDCl$_3$): 8.74 (H⁴, d, 1H, J=8.1 Hz), 8.57 (H⁶, d, 1H, J=8.2 Hz), 7.66 (H$^{8,9,21}$, m, 3H), 7.53 (H⁷, t, 1H, J=8.2 Hz), 7.39 (H³, d, 1H, J=8.1 Hz), 7.33 (H¹⁵, br.s, 2H), 4.51 (H¹⁶, 2H, p, J=7.1 Hz), 4.13 (H¹⁹, q, 4H, J=7.1 Hz), 3.93 (H¹⁰, m, 2H), 3.15 (H$^{11,11',12,12',13}$, m, 20H) 1.41 (H¹⁷, t, 4H, J=7.1 Hz), 1.24 (H²⁰, q, 6H, J=7.1 Hz); δ$_c$ (CDCl$_3$) 180.5 (C⁵), 173.3 (C¹⁸), 170.4 (C¹⁴), 162.4 (C²), 158.6 (C¹), 138.7 (C⁴), 137.0 (C⁴'), 133.4 (C⁹), 130.2 (C⁶), 129.1 (C⁶'), 127.3 (C⁷), 126.8 (C⁸), 125.5 (C⁹'), 122.4 (C³), 61.7 (C¹⁹), 60.6 (C¹⁰), 56.0 (C¹³), 54.2, 53.7, 53.0, 47.0 (C$^{11,11',12,12'}$), 48.4 (C¹⁶), 18.2 (C¹⁸), 14.4 (C²⁰), m/z (HRMS⁺) 712.3484 (M+H)⁺ (C$_{35}$H$_{50}$O$_7$N$_7$S requires 712.3487) R$_f$ 0.36 (alumina, DCM– 5% MeOH).

[EuL¹](CF$_3$SO$_3$)$_3$

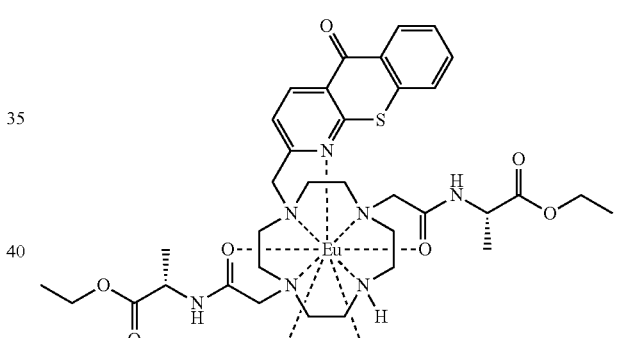

(SS)-1,7-Bis(ethoxycarbonyl-2-ethylcarbamoylmethyl)-4-[(1-azathiaxanthone)-2-methyl]-1,4,7,10-tetraazacyclododecane (18 mg, 25 μmol) was added to Eu(CF$_3$SO$_3$)$_3$ (1 eq., 16 mg) and the solids dissolved in dry MeCN (3 mL) and the reaction left to stir at 80° C. for 74 h. After the reaction was cooled to room temperature, the solvents were removed under reduced pressure and the remaining residue was dissolved in 0.1 mL dry MeCN and the mixture was dropped onto anhydrous Et$_2$O which resulted in precipitation of the title compound as a triflate salt. The precipitate was spinned out and dissolved in 5 ml H$_2$O:MeOH (3:1) The pH was then adjusted carefully to 10 by addition of conc. NaOH solution (in order to remove the excess Eu as Eu(OH)$_3$) resulting in a white precipitate, whish was removed by centrifugation. The pH was adjusted back to neutral with aqueous HCL and the mixture lyophilised to give a bright yellow solid contained approx 2% NaCl as a result of pH adjustment (16 mg, 11.5 μmol). m/z (HRMS⁺) 1162.1618 (M+2CF$_3$SO$_3$)⁺ (C$_{35}$H$_{49}$O$_7$N$_7$SEu(CF$_3$SO$_3$)$_2$ requires 1162.1667); λ$_{max}$ (H$_2$O) 380 (4070 dm$^3$mol$^{-1}$cm$^{-1}$); τ$^{Eu}_{(H2O, pH=7.4)}$: 0.24 ms, τ$^{Eu}_{(D2O, pD=7.1)}$: 0.56 ms; φ$^{Eu}_{(pH=7.4)}$=4.4%

Example 6

Synthesis of [Eu.L³]

(SS)-1,7-Bis(carboxy-2-ethylcarbamoylmethyl)-4-[(1-azathiaxanthone)-2-methyl]-1,4,7,10-tetraazacyclododecane

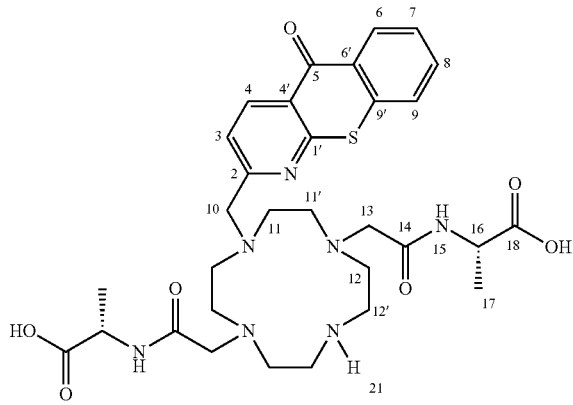 [SMILES: C[C@H](NC(=O)CN1CCNCCN(CC(=O)N[C@@H](C)C(=O)O)CCN(Cc2ccc3c(=O)c4ccccc4sc3n2)CC1)C(=O)O]

Freshly made aqueous KOD solution (2.5 mL, 0.1 M) was added to (SS)-1,7-bis(ethoxycarbonyl-2-ethylcarbamoylmethyl)-4-[(1-azathiaxanthone)-2-methyl]-1,4,7,10-tetraazacyclododecane (61 mg, 86 μmol). The reaction mixture was kept under argon at room temperature and progress was monitored by NMR. After 6 h no ethyl group signals were observed in the ¹H-NMR spectrum. The pH of the mixture was increased (pH≈6) with conc. HCl and the solution loaded onto a DOWEX 50X4-100 strong cation exchange resin. The column was eluted with water→10% NH₄OH and the fractions were analysed by ¹H-NMR. The fractions were combined and lyophilised to yield the title compound as a pale orange oil (43 mg, 66 μmol, 77%), which was used for complexation immediately. $\delta_H$ (D₂O): 8.17 (H⁴, br.d, 1H), 7.98 (H⁶, br.d, 1H), 7.47 (H⁷, br.t, 1H), 7.25 (H$^{8,9,3,15,21}$, m, 7H), 4.02 (H¹⁶, m, 2H, J=8.0 Hz), 3.73 (H¹⁰, br.s, 2H), 3.10 (H$^{111,11',12,12',13}$, m, 20H), 1.14 (H¹⁷, d, 6H, J=7.5 Hz).

[EuL³(OAc)]

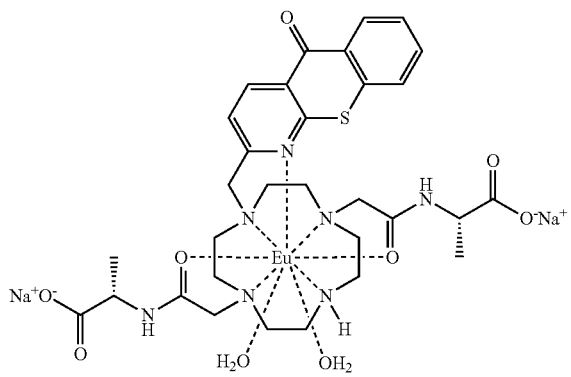

(SS)-1,7-Bis(carboxy-2-ethylcarbamoylmethyl)-4-[(1-azathiaxanthone)-2-methyl]-1,4,7,10-tetraazacyclododecane (43 mg, 66 μmol) was added to Eu(OAc)₃.4H₂O (1.2 eq., 33 mg) and the solids dissolved in 2.5 mL H₂O:MeOH (5:1). The pH was carefully adjusted to 5 by addition of acetic acid and the reaction left to stir at 75° C. for 60 h. After the reaction was cooled to room temperature, The pH was then adjusted carefully to 10 by addition of conc. NaOH solution (in order to remove excess europium as Eu(OH)₃) resulting in a white precipitate removed via centrifugation. The pH was adjusted back to neutral with acetic acid and the sample lyophilised to give a bright yellow solid contained about 2% NaOAc as a result of pH adjustment (20 mg, 22 μmol). m/z (HRMS⁺) 890.2004 (M+Na+OAc) (C₃₁H₄₁O₇N₇SEuNaCH₃COO requires 890.2031); $\lambda_{max}$ (H₂O) 380 (4070 dm³mol⁻¹cm⁻¹); $\tau^{Eu}_{(H2O, pH=7.2)}$: 0.24 ms, $\tau^{Eu}_{(D2O, pD=7.0)}$: 0.70 ms; $\phi^{Eu}_{(pH=7.4)}$=1.2%

Example 7

Synthesis of [Eu.L⁴]

(SS)-1,7-Bis(carboxy-2-ethylcarbamoylphenyl)-4-[(1-azathiaxanthone)-2-methyl]-1,4,7,10-tetraazacyclododecane

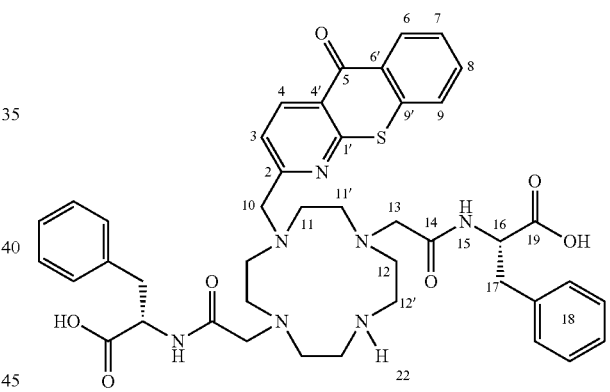

Freshly made aqueous KOD solution (2.5 mL, 0.1 M) was added to (SS)-1,7-bis(ethoxycarbonyl-2-ethylcarbamoylphenyl)-4-[(1-azathiaxanthone)-2-methyl]-1,4,7,10-tetraazacyclododecane (51 mg, 59 μmol) with 0.3 mL CD₃OD. The reaction mixture was kept under argon at room temperature and progress was monitored by NMR. After 10 h ethyl group signals were observed in the ¹H-NMR spectrum. The pH of the mixture was increased (pH≈6) with conc. HCl and the solution loaded onto a DOWEX 50X4-100 strong cation exchange resin. The column was eluted with water→10% NH₄OH and the fractions were analysed by ¹H-NMR. The fractions were combined and lyophilised to yield the title compound as a pale orange oil (25 mg, 32 μmol, 54%), which was used for complexation reaction immediately. $\delta_H$ (D₂O) 8.22 (H⁴, br.s., 1H), 7.94 (H⁶, br.s., 1H), 7.00 (H$^{3,7,8,9,15,18,21}$, m, 17H), 4.63 (H¹⁶, m, 2H), 4.22 (H$^{10,20}$, m, 6H), 2.76 (H$^{11,11',12,12',13,17}$, m, 24H)

[EuL⁴](OAc)

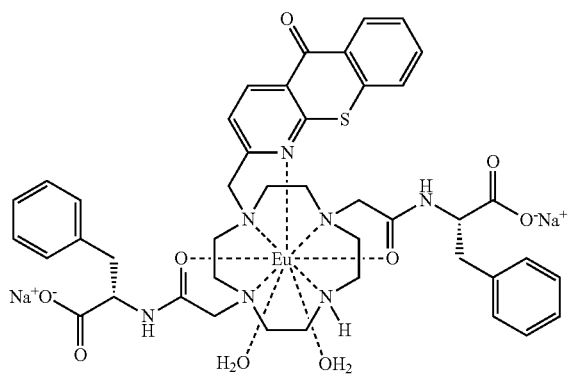

(SS)-1,7-Bis(carboxy-2-ethylcarbamoylphenyl)-4-[(1-azathiaxanthone)-2-methyl]-1,4,7,10-tetraazacyclododecane (25 mg, 32 μmol) was added to Eu(OAc)$_3$.4H$_2$O (1.1 eq., 16 mg) and the solids dissolved in 2.5 mL H$_2$O:MeOH (5:1). The pH was carefully adjusted to 5 by addition of acetic acid and the reaction left to stir at 75° C. for 64 h. After the reaction was cooled to room temperature, The pH was then adjusted carefully to 10 by addition of conc. aqueous NaOH solution (in order to remove excess europium as Eu(OH)$_3$) resulting in a white precipitate removed via centrifugation. The pH was adjusted back to neutral with acetic acid and the sample lyophilised to give a bright yellow solid solid contained about 2% NaOAc as a result of pH adjustment (20 mg, 22 μmol). m/z (HRMS$^+$) 1034.2991 (M+Me+OAc) (C$_{43}$H$_{49}$O$_7$N$_7$SEuCH$_3$COO (as a mono Me-ester) requires 1034.2994); $\lambda_{max}$ (H$_2$O) 380 (4070 dm$^3$mol$^{-1}$cm$^{-1}$); $\tau^{Eu}_{(H2O, pH=7.4)}$: 0.24 ms, $\tau^{Eu}_{(D2O, pD=7.0)}$: 0.70 ms; $\phi^{Eu}_{(pH=7.4)}$=0.8%.

Example 8

Synthesis of [Eu.L⁷] (Comparative Example)

1,7-Bis(α-glutarate)-4-[(1-azathiaxanthone)-2-methyl]-1,4,7,10-tetraaza-cyclododecane

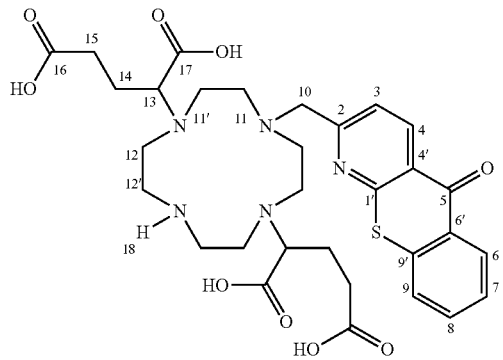 [SMILES: O=C(O)CCC(C(=O)O)N1CCNCCN(C(CCC(=O)O)C(=O)O)CCN(Cc2ccc3c(=O)c4ccccc4sc3n2)CC1]

Freshly made aqueous KOD solution (2.5 mL, 0.1 M) was added to 1,7-bis(α-dimethylglutarate)-4-[(1-azathiaxanthone)-2-methyl]-1,4,7,10-tetraaza-cyclododecane (70 mg, 98 μmol). The reaction mixture was kept under argon at room temperature and progress was monitored by NMR. After 8 h no methyl group signals were observed in the $^1$H-NMR spectrum. The pH of the mixture was decreased (pH≈6) with conc. HCl and the solution loaded onto a DOWEX 50X4-100 strong cation exchange resin. The column was eluted with water→10% NH$_4$OH and the fractions were analysed by 1H-NMR. The fractions were combined and lyophilised to yield the title compound as a dark yellow solid (38 mg, 57 μmol, 58%), which was used in a complexation reaction immediately. $\delta_H$ (D$_2$O): mainly broad overlapping signals; no Me groups in $^1$H-NMR, $\delta_H$ (D$_2$O) 8.33 (1H, d, J 8.0 Hz, H⁴), 8.11 (1H, d, J 8.0 Hz, H⁶), 7.41 (5H, m, H$^{8,9,3,7,18}$), 3.53 (2H, s, H$^{10}$), 3.09 (18H, br.m, H$^{11,11',12,12',13}$), 1.90 (8H, m, H$^{14,15}$); m/z (ESMS$^{31}$) 656 (M−H)⁻.

[NaEuL⁷]

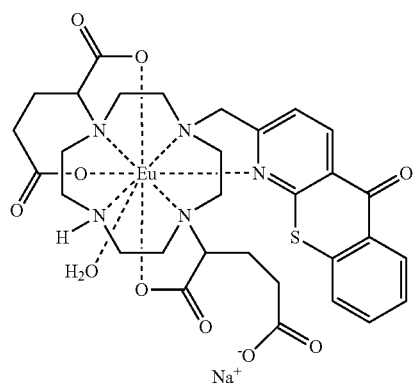

1,7-Bis(α-glutarate)-4-[(1-azathiaxanthone)-2-methyl]-1,4,7,10-tetraaza-cyclododecane (33 mg, 50 μmol) was added to Eu(CH$_3$CO$_2$)$_3$ (1.1 eq., 23 mg) and the solids dissolved in a H$_2$O:MeOH (10:1 mL). The pH was carefully adjusted to 5 by addition of acetic acid and the reaction left to stir at 80° C. for 72 h. After the reaction was cooled to room temperature, the solvents were removed under reduced pressure and the remaining residue was dissolved in 5 mL H$_2$O. The pH was then adjusted carefully to 10 by addition of conc. aqueous NaOH solution (in order to remove the excess europium as Eu(OH)$_3$) resulting in a white precipitate, removed via centrifugation. The pH was adjusted back to neutral with acetic acid and the mixture lyophilised to give a bright yellow solid contained about 2% NaOAc as a result of pH adjustment (33 mg, 37 μmol). m/z (HRMS$^−$) 821.1669, (M+Me)$^+$ 889.1474 (M+Na+OAc)$^+$ (C$_{31}$H$_{36}$O$_9$N$_5$SEu mono Me-ester requires 821.1675, C$_{31}$H$_{36}$O$_9$N$_5$SEuNaCH$_3$COO requires 889.1471); $\lambda_{max}$ (H$_2$O) 380 (4070 dm$^3$mol$^{-1}$cm$^{-1}$); $\tau^{Eu}_{(H2O,pH=3.0)}$: 0.29 ms, $\tau^{Eu}_{(H2O, pH=8.0)}$: 0.30 ms; $\tau^{Eu}_{(D2O, pD=2.6)}$: 0.59 ms, $\tau^{Eu}_{(D2O, pD=7.6)}$: 0.63 ms; $\phi^{Eu}_{(pH=3.0)}$=1.2%, $\phi^{Eu}_{(pH=8.0)}$= 1.2%

HPLC Analysis/Purification

Reverse phase HPLC analyses were performed at 298 K using a Perkin Elmer System with a 4.6×20 mm 4μ Phenomenex Synergi Fusion RP 80i analytical column. In each case an H$_2$O+0.1% HCOOH/MeCN+0.1% HCOOH solvent system was used (gradient elution) with a run time of 20 minutes. In each case, a single major product was observed in >95% purity using a diode array UV-Vis detector operating at 340 nm, which corresponds to the absorption band of the appropriate azaxanthone sensitizing moiety (analysis was also undertaken at 280 nm). Such behaviour indicated that each of the species that were eluted bear this chromophore. A fluorescence detector was also connected to the HPLC, monitoring eluent from the column at a wavelength corresponding to the Eu centred emission (616 nm); again emission was seen for each of these peaks, suggesting that each peak corresponding to a chromophore bound species that was also coordinated to Eu.

| | Gradient elution programme for HPLC analysis. | | | |
|---|---|---|---|---|
| Time (min) | Flow (mL/min) | $H_2O$ (+0.1% HCOOH) (%) | MeCN (+0.1% HCOOH) (%) | Gradient |
| 3.0 (prior injection) | 1 | 100 | 0 | 0 |
| 1.0 | 1 | 100 | 0 | 0 |
| 10.0 | 1 | 0 | 100 | 1 |
| 5.0 | 1 | 0 | 100 | 0 |
| 0.5 | 1 | 100 | 0 | 1 |
| 5.0 | 1 | 100 | 0 | 0 |

FIGS. 1A through 1I show LC chromatograms following HPLC purification of $EuL^8$, $EuL^9$, $EuL^1$, $EuL^2$, $EuL^3$, $EuL^4$, $EuL^7$, $EuL^5$ and $EuL^6$, respectively.

Analyses

A. Determination of Binding Constants of Complexes of the Invention and Comparative Complexes Affinity constants for lactate, citrate and bicarbonate with $[Eu.L^1]^{3+}$-$[Eu.L^9]^-$ were determined in saline solution (298 K, 0.1 M NaCl, 4 mM KCl, 0.9 mM $Na_2HPO_4$, pH 6.55), observing the change in the intensity ratio of the $Eu^{3+}$ emission bands at 616/686 nm as a function of added anion, and are presented in Table 1 below. With lactate and citrate, measurements were also made in a 'simulated prostate fluid' background, prior to analyses in prostate fluid clinical samples. This medium contained various $MCl_2$ salts (M=Mg, Ca, Zn, $C_{tot}^{M2+}$=11 mM), human serum albumin (0.3 mM) and 3 mM $NaHCO_3$, Table I. The added $M^{2+}$ salts not only compete for the oxy-anion but also appear to stabilise certain ternary [Eu.L(citrate)] adducts. For example, with $[Eu.L^2]^{3+}$, titrations of citrate (pH 7.4, 0.1 HEPES, 0.1 M NaCl, 0.9 mM $NaH_2PO_4$, 30 mM $NaHCO_3$ and 2.3 mM sodium lactate) in the absence and presence of 2 mM $MCl_2$ (M=Ca, Zn and Mg) revealed an apparent affinity constant that increased by about two log units.

TABLE 1

Comparison of apparent binding constants (log K) for europium(III) complexes with the stated anion (298K, 20 μM complex, $\lambda_{exc}$ 380 (azathiaxanthone) or 337 (azaxanthone) nm, pH 6.55) in saline solution[a] and in a simulated prostate fluid background[b] (values given in italics), with standard deviations.

| Complex | citrate | lactate | bicarbonate |
|---|---|---|---|
| $[Eu.L^1]^{3+}$ | 5.26(03) | 3.31(02) | 2.81(02) |
| | [5.20](02) | [3.41](03) | |
| $[Eu.L^2]^{3+}$ | 5.22(02) | 3.27(01) | 3.07(01) |
| | [4.88](04) | [2.97](03) | |
| $[Eu.L^3]^+$ | 4.58(03) | 2.94(03) | 2.55(03) |
| | [4.51](01) | [3.20](02) | |
| $[Eu.L^4]^+$ | 4.01(02) | 2.79(04) | 2.23(02) |
| | [4.20](03) | [2.82](03) | |
| $[Eu.L^5]^+$ | 4.19(02) | 3.08(02) | 2.14(02) |
| | [3.89](03) | [3.43](05) | |
| $[Eu.L^6]^+$ | 4.36(01) | 3.49(01) | 2.80(01) |
| | [3.97](04) | [3.82](01) | |
| $[Eu.L^7]^-$ | 2.52(02) | 2.46(02) | 2.11(05) |
| | [3.12](02) | [2.90](01) | |
| $[Eu.L^8]^-$ | 2.54(03) | 3.03(01) | 1.27(02) |
| | [1.54](03) | [2.65](02) | |

TABLE 1-continued

Comparison of apparent binding constants (log K) for europium(III) complexes with the stated anion (298K, 20 μM complex, $\lambda_{exc}$ 380 (azathiaxanthone) or 337 (azaxanthone) nm, pH 6.55) in saline solution[a] and in a simulated prostate fluid background[b] (values given in italics), with standard deviations.

| Complex | citrate | lactate | bicarbonate |
|---|---|---|---|
| $[Eu.L^9]^-$ | 1.69(01) | 3.18(02) | 1.23(03) |
| | [2.02](02) | [3.33](01) | |

[a]contains: 0.1M NaCl, 4 mM KCl, 0.1M HEPES and 0.9 mM $NaH_2PO_4$
[b]contains: 0.1M NaCl, 4 mM KCl, 4 mM $CaCl_2$, 2 mM $ZnCl_2$, 5 mM $MgCl_2$, 0.3 mM HSA, 3 mM $NaHCO_3$ and 0.1M HEPES.

Pronounced citrate/lactate selectivity was observed with the positively charged complexes, e.g. for $[Eu.L^3]^+$, the ratio of affinity constants is 42:1. Lactate binding is preferred with the more sterically demanding mono-anionic complexes and for $[Eu.L^9]^-$, the lactate/citrate ratio was 30:1. These complexes were selected for further study (see sections B and C below), analysing the citrate or lactate content of serum, urine, saliva, seminal and prostate fluid samples using the luminescence method, comparing data obtained to measurements made using enzyme kits (obtained from Megazyme Ltd., Ireland).

B. Lactate Analysis in Various Biofluids

For lactate (and citrate) analyses using the Eu emission method, a calibration curve is first determined in an appropriate background medium, allowing the working range of the measurement to be defined. Thus, in a simulated prostate fluid background containing 0.3 mM HSA, 0.1 M NaCl, 4 mM KCl, 3 mM $NaHCO_3$, 4 mM $CaCl_2$, 2 mM $ZnCl_2$, 5 mM $MgCl_2$ (pH 6.5, 0.1 M HEPES), FIG. 1, modulation of Eu emission (10 μM concentration) is evident over the lactate concentration range 0 to 1 mM. Typically, a 5 μL sample of fluid, (seminal or prostate) is diluted by a factor of 10, filtered through a 10 kD cut-off filter, and analysed in a 50 μL it optical cuvette ($\lambda_{exc}$ 336 nm). The intensity ratio of the 692/619 or 613/622 or 613/619 emission bands in $[Eu.L^9]^-$ is measured and the lactate concentration deduced by reference to the calibration curve. Samples of lactate in urine (3.5 mM), seminal fluid (3.8 mM) prostate fluid (4 mM) and reconstituted human serum (1.9 mM) were found to be within 10% of the concentration deduced enzymatically. In saliva, each method gave a zero reading for lactate (±0.2 mM).

Figure 3:
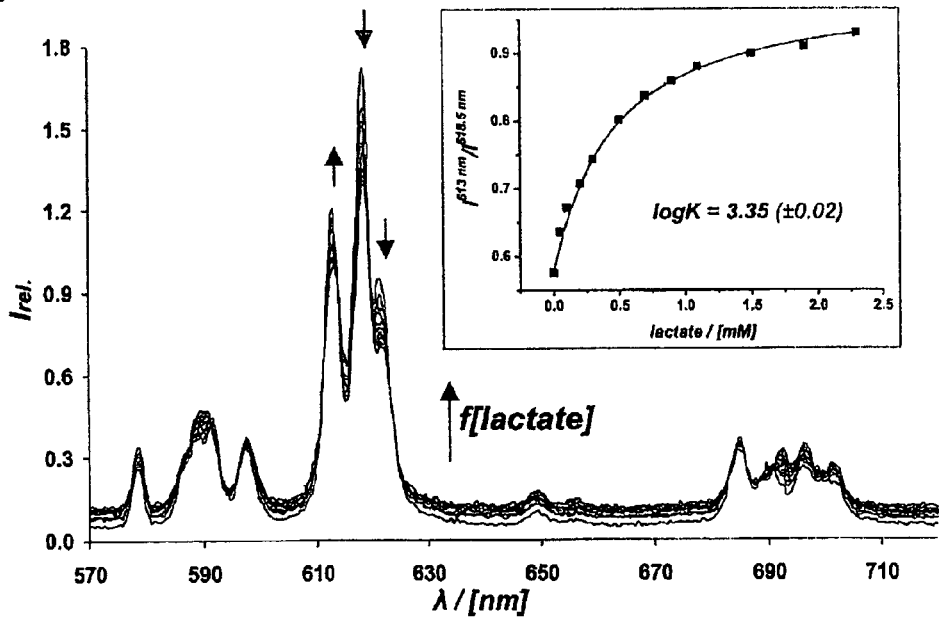
FIG. 3 shows high resolution Eu$^{3+}$ emission bands obtained by exciting mixtures of varying concentrations of sodium lactate with a europium-containing complex of the invention ([EuL$^9$]$^-$) (pH 6.5, 0.1 M HEPES, $\lambda_{exec}$ 337 nm, 10 μM complex, 0.1 M NaCl, 0.3 mM NaHCO$_3$, 0.4 mM KCl, 0.03 mM HSA, 0.4 mM CaCl$_2$, 0.2 mM ZnCl$_2$, 0.5 mM MgCl$_2$). The insert shows the ratio of two emission emission bands as a function of lactate concentration, with the fit (line) to the data.

Excitation of the Eu(III) complex, $[Eu.L^9]^-$ in solution at 336 (±20) nm leads to an emission spectrum from 580 to 700 nm. The analysis utilises ratiometric detection, by plotting changes in the ratio of up to 4 different wavelengths as a function of lactic acid concentration. Therefore, establishment of a suitable calibration curve and appropriate dilution provides a fast method for the determination of lactate in various fluids or solutions. FIG. 3 shows high resolution Eu emission spectra, of the europium complex $[Eu.L^9]^-$ (pH 6.5, 0.1 M HEPES, 298K, $\lambda_{ex}$=336 nm, $C_{EuL}$=10 μM) as a function of sodium lactate concentration (using ISA Jobin-Yvon Spex Fluorolog-3 luminescence spectrometer), displaying (insert) the calibration curve determined using the stated emission band intensity ratios (613 vs. 618.5 nm) as a function of added sodium lactate.

The precision of the measurement, which is an inherent feature of such a ratiometric assay, generates less than 3% variance in the measured intensity ratio for a given lactate concentration. Analyses were carried out with a typical sample volume of 50 μL requiring about 1 μg of the Eu complex. The sample preparation time and spectral acquisition is quick (<5 min.). A sensitive spectrofluorimeter is required possessing ±1 nm resolution. Inexpensive disposable cuvettes may be used and commercially available buffer solutions were used for dilution (pH 6.5). Analyses have been undertaken for the determination of lactate in a variety of biological samples (plasma, seminal and prostate fluid, urine and saliva), with confirmation of the accuracy of the analysis by comparison with the currently available (Megazyme Ltd., Ireland) enzymatic L-lactic acid assay kit (Table 2).

TABLE 2

Simultaneous analysis of unknown clinical samples (PR, SF, P, S and U referring to Prostate Fluid, Seminal Fluid, Plasma, Saliva and Urine samples respectively); samples were measured in ×10 dilution.

| Sample | [Eu.L$^9$]$^-$ | Enzyme Kit |
|---|---|---|
| PF-13007 | 4.0 ± 0.5 mM | 3.6 ± 0.5 mM |
| SF-R1 | 4.0 ± 0.5 mM | 4.4 ± 0.4 mM |
| P-A | 1.8 ± 0.2 mM | 1.9 ± 0.2 mM |
| S-R1 | 0 mM | 0 mM |
| U-R1 | 1.0 ± 0.5 mM | 1.2 ± 0.2 mM |

C. Determination of Citrate in Biological Fluids Using [Eu.L$^3$]$^+$

Figure 5:
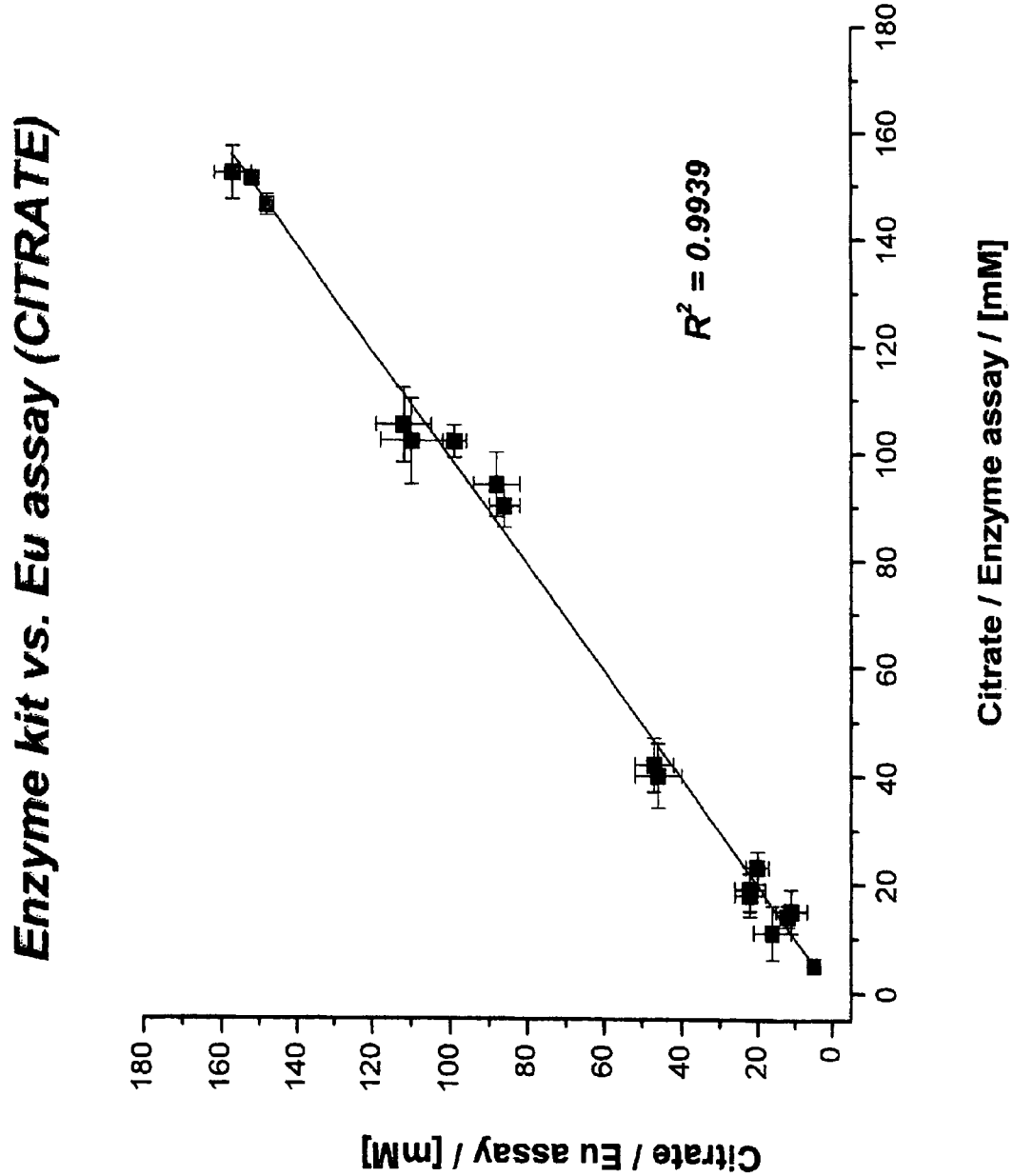
FIG. 5 shows a comparison of citrate concentrations determined in diluted fluid samples, in particular prostate fluid samples, comparing the results obtained according to the present invention with those using a citrate lyase kit, ($R^2$=0.9939).

Similar procedures as described above in connection with the determination of lactate used to analyse for citrate using [Eu.L$^3$]$^+$. In this case, typically a 1 μL sample of prostatic fluid is diluted ×100. To obviate any interference due to changes in lactate concentration in prostate fluid samples, calibration measurements in this case only were made ($\lambda_{exc}$ 365 nm, 10 μs gate time, 50 μL optical cell) in the presence of 0.1 M sodium lactate containing simulated prostate fluid solution. Citrate was determined in fourteen samples of prostate fluid, and values ranging from 12 mM to 160 mM measured, confirmed (±10%) by independent analysis (see FIG. 5) using the citrate lyase enzyme kit, for which the amount of bio-fluid required was 25 times greater. Using similar methods, but with a 10-fold dilution of sample, citrate could be determined in the urine of healthy volunteers (range 3.5 to 5.5 mM (±10%)).

Figure 2:
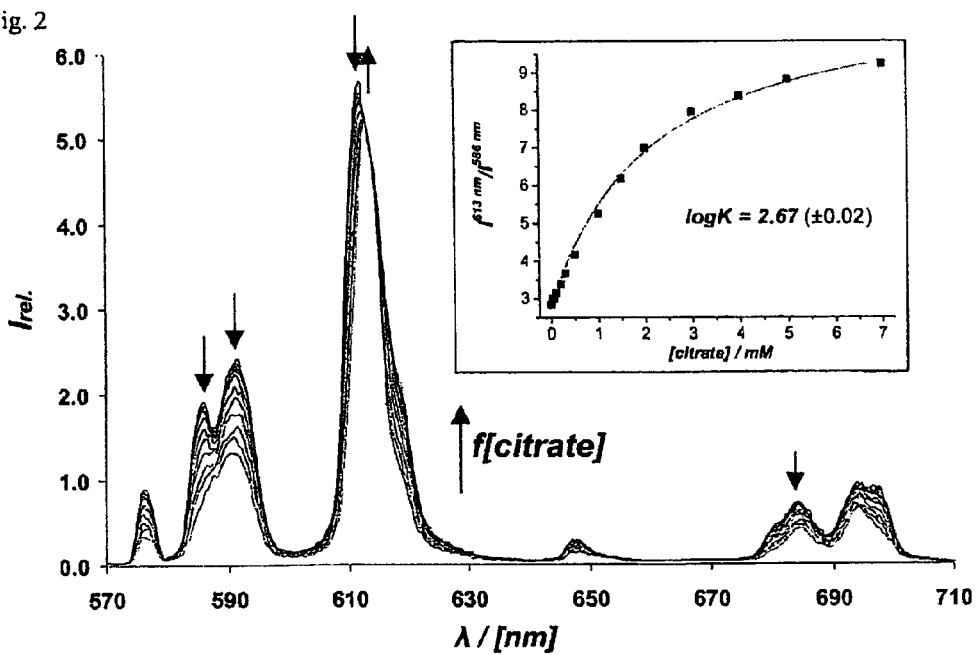
FIG. 2. shows a 50 μs time-gated high resolution Eu emission spectrum obtained by exciting mixtures of varying concentrations of sodium citrate with a europium-containing complex (20 μM) of the invention ([EuL$^3$]$^+$). The other conditions are as described for FIG. 3. below. The insert shows the ratio of two emission bands as a function of citrate concentration, with the fit (line) to the data.
Figure 4:
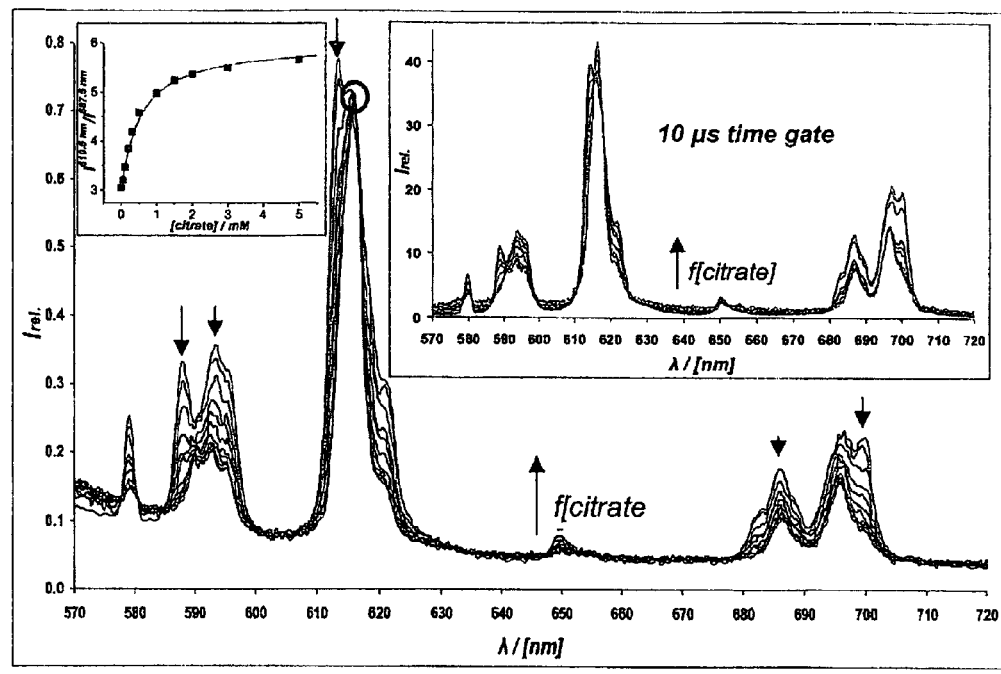
FIG. 4 shows high resolution Eu emission spectra, of the europium complex [Eu.L$^3$]$^+$ (pH 6.5, 0.1 M HEPES, 298K, $\lambda_{ex}$=380 nm, $C_{EuL}$=10 μM) as a function of sodium citrate concentration, displaying (insert left) the calibration curve determined using the given emission band intensity ratios (614 vs. 683 nm) as a function of sodium citrate. (insert right) time gated (10 μs) Eu emission spectra, of the europium complex (pH 6.5, 0.1 M HEPES, 298K, $\lambda_{ex}$=365 nm, $C_{EuL}$=10 μM) as a function of sodium citrate concentration.

The europium complex, [Eu.L$^3$]$^+$ is based on a lanthanide-macrocyclic complex, incorporating an azathiaxanthone antenna group, allowing excitation of the Eu(III)complex in solution at 380 (±25) nm, leading to metal based emission from 580 to 710 nm. The analysis utilises ratiometric detection, plotting changes in the ratio of up to 6 different emission wavelengths as a function of citric acid concentration. Therefore, following establishment of a suitable calibration curve and appropriate sample dilution a fast method is defined for the determination of citrate in various fluids. FIG. 4 shows high resolution Eu emission spectra, of the europium complex [Eu.L$^3$]$^+$ (pH 6.5, 0.1 M HEPES, 298K, $\lambda_{ex}$=380 nm, $C_{EuL}$=10 μM) as a function of sodium citrate concentration, displaying (insert left) the calibration curve determined using the given emission band intensity ratios (614 vs. 683 nm) as a function of sodium citrate. (insert right) time gated (10 μs) Eu emission spectra, of the europium complex (pH 6.5, 0.1 M HEPES, 298K, $\lambda_{ex}$=365 nm, $C_{EuL}$=10 μM) as a function of sodium citrate concentration. FIG. 2 is similar (non inset) but is obtained using a 50 μs time-gate, 20 μm of [EuL$^3$]$^+$, $\lambda_{exc}$=365 nm, 0.1 M NaCl, 0.3 mM NaHCO$_3$, 0.4 mM KCl, 0.03 mM HSA, 0.4 mM CaCl$_2$, 0.2 mM ZnCl$_2$, 0.5 mM MgCl$_2$ and 0.1 M Na lactate.

The precision of the measurement, which is an inherent feature of such a ratiometric assay, allows less than 3% variance in the measured intensity ratio for a given citrate concentration. One analysis in a typical sample volume of 50 μL, requires 1 μg of compound with rapid sample preparation and a fast (3 min.) acquisition time. The sample requirement of the analysis can be as small as 1 μL original fluid, as a 100 times dilution is used with this method. Instrumental requirements are a sensitive spectrofluorimeter possessing ±1 nm resolution (e.g. ISA Jobin-Yvon Spex Fluorolog-3 or Ocean Optics Red Tide Spectrometer), and a commercially available buffer solution for dilution (pH 6.5). As the azathiaxanthone chromophore displays a significant amount of ligand fluorescence, causing interference in the form of a sloping baseline, time gated measurements are preferred for precise calibration. This can be achieved using a time-gated spectrometer. In this case a home-built instrument was used, incorporating a time gating device. Using this instrument, the short-lived fluorescence of the sensitising moiety is eliminated by applying a 10 microsecond time-gate.

Using the calibration curve, citrate concentrations of clinical prostate fluid samples have been successfully differentiated using an appropriate calibration curve.

D. Analyses of Citrate and Lactate in a Variety of Biological Samples (Plasma, Seminal and Prostate Fluid, Urine and Saliva) Using [Eu.L$^3$]$^+$ and [Eu.L$^9$]$^-$ In order to demonstrate the application of [Eu.L$^3$]$^+$ in the analysis of various bio-fluids for citrate, and the application of [Eu.L$^9$]$^-$ in the analysis of various bio-fluids for lactate, analysis of clinical samples with unknown citrate and lactate levels has been undertaken.

To allow a comparison the citrate level in these samples was evaluated using a commercially available (Megazyme Ltd, Ireland) enzymatic citric acid kit. Typical analysis time using [Eu.L$^3$] was 3 minutes with a 50 μL total sample volume (0.5 μL actual bio-fluid content) compared to the 20 min acquisition time and 3 mL sample volume required using the enzyme kit. Values refer to the mean of 3 measurements (s.d. in parenthesis, Table 2 below). Values are plotted in FIG. 5.

Figure 6:
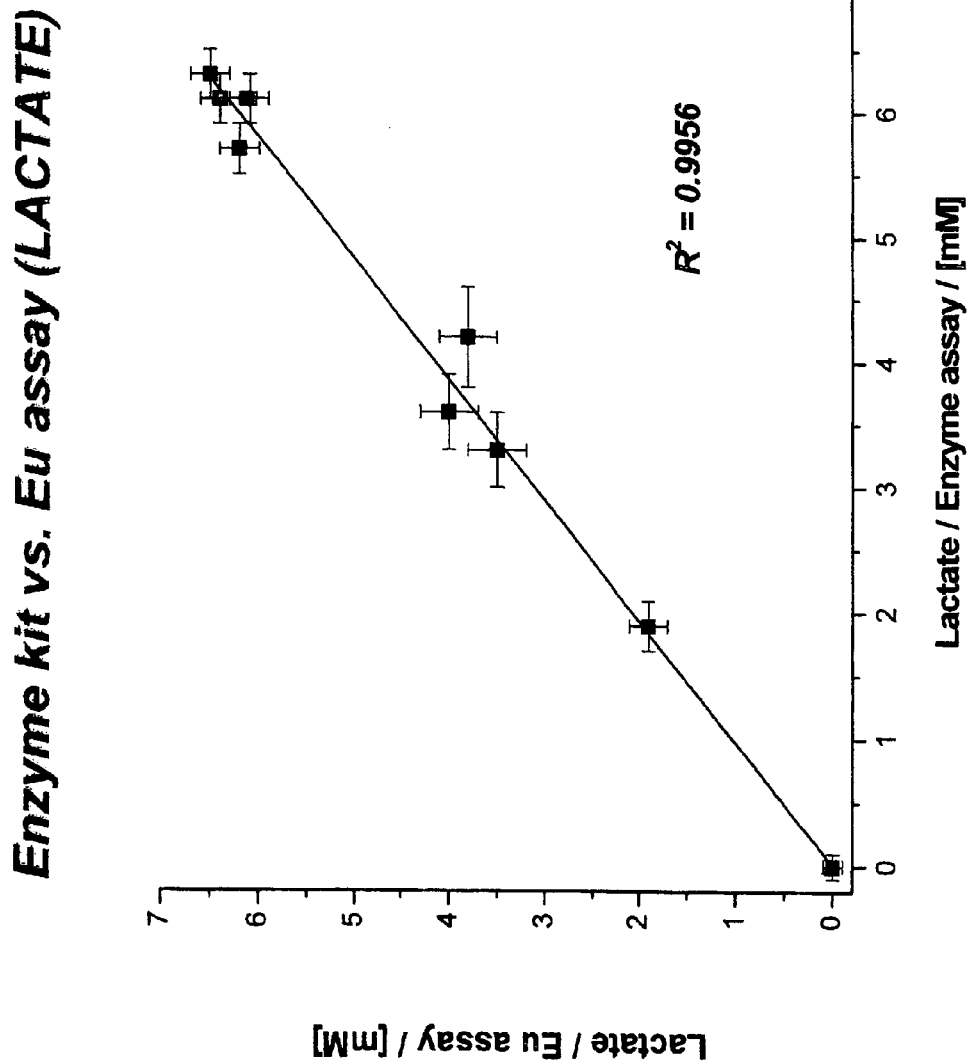
FIG. 6 shows a comparison of lactate concentrations determined in diluted fluid samples, in particular prostate fluid samples, comparing the results obtained according to the present invention with those using a L-Lactate dehydrogenase kit, ($R^2$=0.9956).

Analyses have also been undertaken for the determination of lactate in a variety of biological samples (plasma, seminal and prostate fluid, urine and saliva), with confirmation of the accuracy of the analysis by comparison with the currently available (Megazyme Ltd., Ireland) enzymatic L-lactic acid assay kit (Table 2). Values are plotted in FIG. 6.

TABLE 2

Samples 13007, 103007, 103009, 1-N, 3-n and 1-15 all of prostatic fluid;
Seminal F = seminal fluid; for citrate measurements: ×200 dilution;
for lactate measurements ×10 dilution

| Sample No. | Citrate assay using the present invention | Lactate assay using the present invention | L-Lactate dehidrogenase kit | Citrate lyase kit |
|---|---|---|---|---|
| 13007 | 11 ± 2 mM | 4.0 ± 0.5 mM | 3.6 ± 0.5 mM | 15 ± 3 mM |
| 103007 | 110 ± 10 mM | 2.5 ± 0.5 mM | — | 102 ± 5 mM |

TABLE 2-continued

Samples 13007, 103007, 103009, 1-N, 3-n and 1-15 all of prostatic fluid; Seminal F = seminal fluid; for citrate measurements: ×200 dilution; for lactate measurements ×10 dilution

| Sample No. | Citrate assay using the present invention | Lactate assay using the present invention | L-Lactate dehydrogenase kit | Citrate lyase kit |
|---|---|---|---|---|
| 103009 | 157 ± 10 mM | 4.0 ± 0.5 mM | — | 152 ± 5 mM |
| I-N | 15 ± 3 mM | 3.1 ± 0.5 mM | — | — |
| 3-N | 110 ± 10 mM | 6.0 ± 0.5 mM | — | — |
| 1 | 20 ± 3 mM | 6.4 ± 0.2 mM | 6.1 ± 0.2 mM | 23 ± 3 mM |
| 2 | 16 ± 2 mM | 6.5 ± 0.2 mM | 6.3 ± 0.2 mM | 11 ± 3 mM |
| 3 | 12 ± 2 mM | 6.1 ± 0.2 mM | 6.1 ± 0.2 mM | 14 ± 3 mM |
| 4 | 86 ± 5 mM | — | — | 90 ± 5 mM |
| 5 | 148 ± 5 mM | — | — | 146 ± 5 mM |
| 6 | 99 ± 5 mM | — | — | 102 ± 5 mM |
| 7 | 46 ± 5 mM | 6.2 ± 0.2 mM | 5.7* ± 0.2 mM | 40 ± 5 mM |
| 8 | 152 ± 5 mM | — | — | 151 ± 5 mM |
| 9 | 88 ± 5 mM | — | — | 94 ± 5 mM |
| 10 | 22 ± 3 mM | 2.7 ± 0.2 mM | — | 18 ± 3 mM |
| 13 | 112 ± 5 mM | — | — | 105 ± 5 mM |
| 15 | 22 ± 3 mM | 5.4 ± 0.2 mM | — | 19 ± 3 mM |
| SeminalF | 47 ± 5 mM | 3.8 ± 0.3 mM | 4.4# ± 0.5 mM | 42 ± 5 mM |
| Urine | 5 ± 2 mM | 3.5 ± 0.3 mM | 3.3 ± 0.3 mM | 5 ± 1 mM |
| Plasma | — | 1.9 ± 0.2 mM | 1.9 ± 0.2 mM | — |
| Saliva | — | 0mM | 0mM | — |

The invention claimed is:

1. A compound of formula (I):

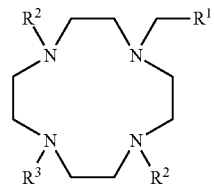

(I)

wherein:

$R^1$ is an optionally substituted 2-(1-azathiaxanthone);

each $-R^2$ is independently of the formula $-CH_2-C(=O)-R^4$, wherein $R^4$ is an amino acid or a salt thereof, attached to the remainder of $R^2$ through the nitrogen atom of the amino group of the amino acid; and $R^3$ is hydrogen or a $C_{1-6}$ alkyl group.

2. The compound of claim 1 wherein the 2-(1-azathiaxanthone) is unsubstituted or is substituted one or more times at one or more of positions 3, 7, 8 or 9 with substituents independently selected from the group consisting of alkyl, acylamino, amino, carboxylate and ester.

3. The compound of claim 1 wherein each $R^4$ is independently a naturally occurring amino acid, or salt thereof, attached to the remainder of the $R^2$ to which it is attached through the nitrogen atom of the α-amino group.

4. The compound of claim 3 wherein each $-R^4$ is independently $-N(H)C(H)(CH_2Ph)COOH$, or a salt thereof, or $-N(H)C(H)(CH_3)COOH$, or a salt thereof.

5. The compound of claim 1 wherein each $R^2$ is the same.

6. The compound of claim 1 wherein $R^3$ is hydrogen.

7. The compound of claim 1 wherein the compound of formula (I) is of either of the following formulae:

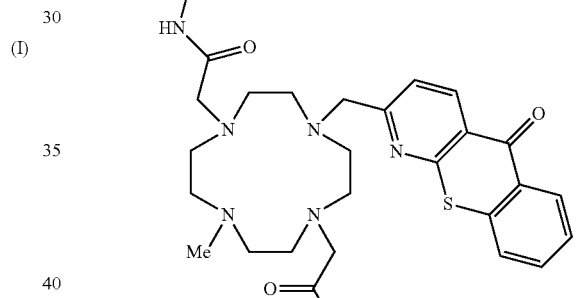

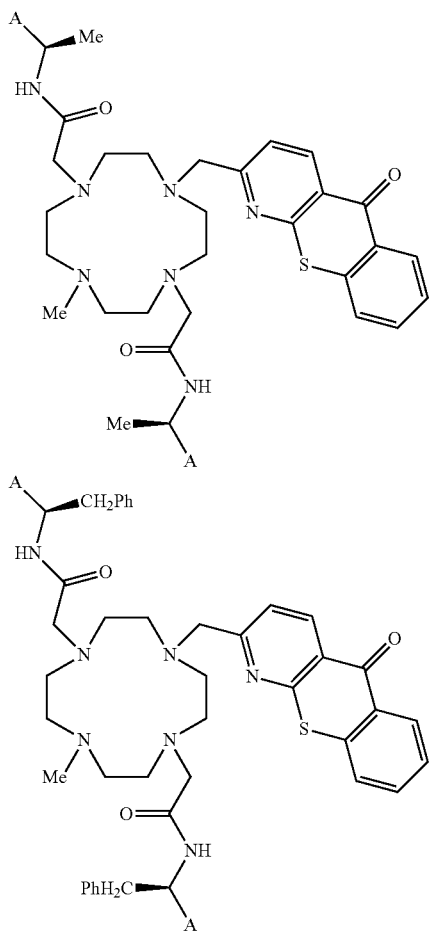

wherein each -A is $-CO_2H$, or a salt thereof.

8. The compound of claim 1 wherein the compound of formula (I) is of either of the following formulae:

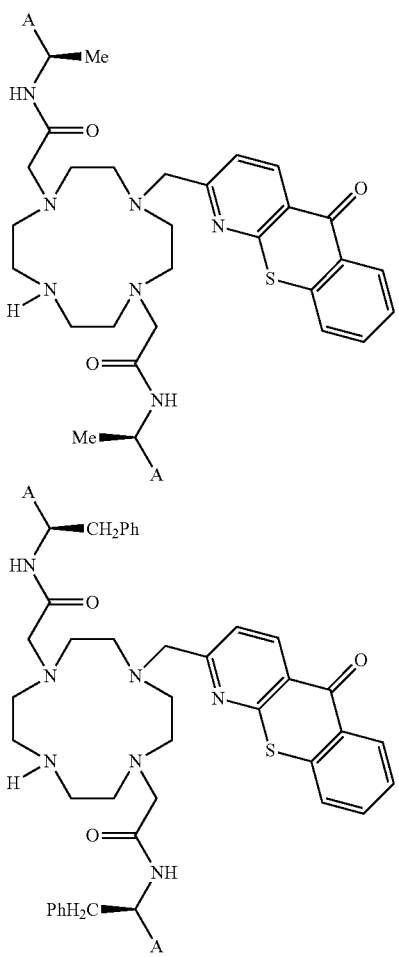

wherein each -A is —CO$_2$H, or a salt thereof.

9. A complex comprising:
a compound of formula (I)

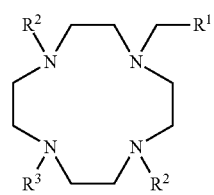

wherein,
R$^1$ is an optionally substituted 2-(1-azathiaxanthone);
each —R$^2$ is independently of the formula —CH$_2$—C(=O)—R$^4$, wherein R$^4$ is an amino acid or a salt thereof, attached to the remainder of R$^2$ through the nitrogen atom of the amino group of the amino acid; and
R$^3$ is hydrogen or a C$_{1-6}$ alkyl group; and
a lanthanide (III) ion.

10. The complex of claim 9 wherein the lanthanide (III) ion is europium (III) or terbium (III).

11. The complex of claim 9 wherein the lanthanide (III) ion is europium (III).

12. The complex of claim 9 wherein the 2-(1-azathiaxanthone) is unsubstituted or is substituted one or more times at one or more of positions 3, 7, 8 or 9 with substituents independently selected from the group consisting of alkyl, acylamino, amido, carboxylate and ester.

13. The complex of claim 9 wherein each R$^4$ is independently a naturally occurring amino acid, or salt thereof, attached to the remainder of the R$^2$ to which it is attached through the nitrogen atom of the α-amino group.

14. The complex of claim 13 wherein each —R$^4$ is independently —N(H)C(H)(CH$_2$Ph)COOH, or a salt thereof, or —N(H)C(H)(CH$_3$)COOH, or a salt thereof.

15. The complex of claim 9 wherein each R$^2$ is the same.

16. The complex of claim 9 wherein R$^3$ is hydrogen.

17. The complex of claim 9 wherein the compound of formula (I) is of either of the following formulae:

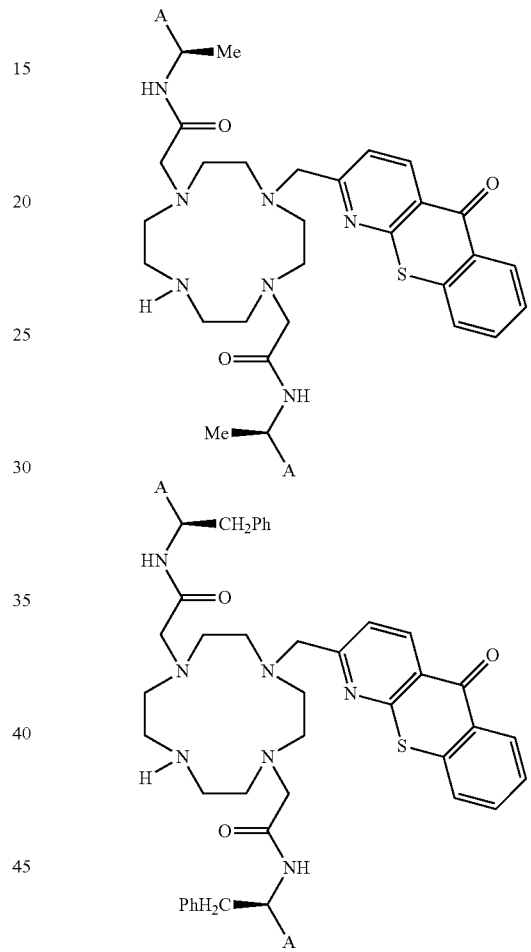

wherein each -A is —CO$_2$H, or a salt thereof.

18. A method of analyzing citrate present in a sample of interest, the method comprising:
contacting the sample of interest with a complex comprising
a compound of formula (I) and a lanthanide (III) ion, wherein formula (I) is as follows

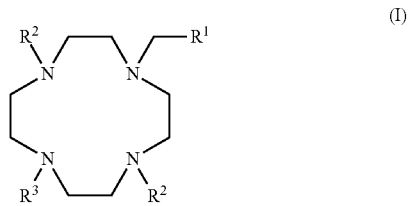

wherein,
R¹ is an optionally substituted 2-(1-azathiaxanthone);
each —R² is independently of the formula —CH₂—C(=O)—R⁴, wherein R⁴ is an amino acid or a salt thereof, attached to the remainder of R² through the nitrogen atom of the amino group of the amino acid; and
R³ is hydrogen or a $C_{1-6}$ alkyl group;
exciting the azathiaxanthone; and
determining the quantity or concentration of any citrate in the sample of interest by analysis of the modulation in one or more emission bands resultant from the exciting where citrate is present.

19. A method of, or for use in, the diagnosis of prostate cancer comprising:
   (i) obtaining a liquid sample from a subject;
   (ii) optionally diluting the liquid sample; and
   (iii) practicing a method as defined in claim 18, wherein the liquid sample or the diluted liquid sample constitutes the sample of interest.

20. A method of, or for use in, the diagnosis of a renal anomaly comprising:
   (i) obtaining a liquid sample from a subject;
   (ii) optionally diluting the liquid sample; and
   (iii) practicing a method as defined in claim 18, wherein the liquid sample or the diluted liquid sample constitutes the sample of interest.

21. The method of claim 19 wherein the liquid has been previously obtained from the subject.

22. The method of claim 18 wherein the 2-(1-azathiaxanthone) is unsubstituted or is substituted one or more times at one or more of positions 3, 7, 8 or 9 with substituents independently selected from the group consisting of alkyl, acylamino, amido, carboxylate and ester.

23. The method of claim 18 wherein each R⁴ is independently a naturally occurring amino acid, or salt thereof, attached to the remainder of the R² to which it is attached through the nitrogen atom of the α-amino group.

24. The method of claim 23 wherein each —R⁴ is independently —N(H)C(H)(CH₂Ph)COOH, or a salt thereof, or —N(H)C(H)(CH₃)COOH, or a salt thereof.

25. The method of claim 18 wherein each R² is the same.

26. The method of claim 18 wherein R³ is hydrogen.

27. The method of claim 18 wherein the compound of formula (I) is of either of the following formulae:

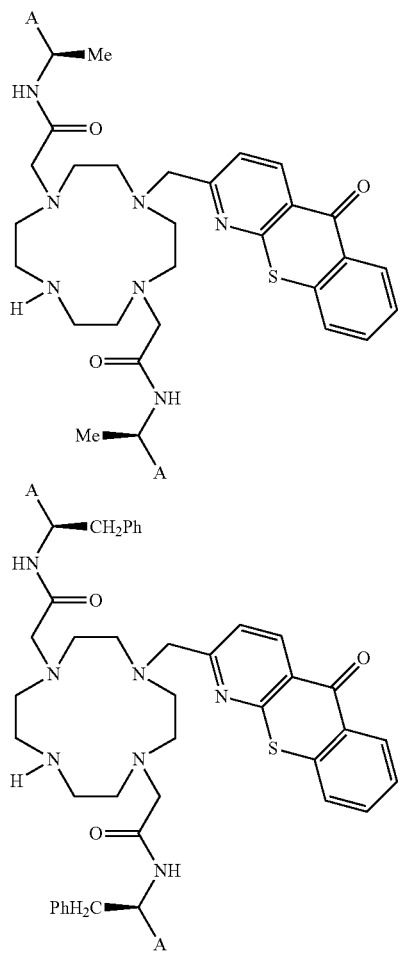

wherein each -A is —CO₂H, or a salt thereof.

28. The method of claim 18 wherein the lanthanide (III) ion is europium (III) or terbium (III).

29. The method of claim 18 wherein the lanthanide (III) ion is europium (III).

* * * * *